United States Patent [19]
Okasinski et al.

[11] Patent Number: 5,888,772
[45] Date of Patent: *Mar. 30, 1999

[54] DNA ENCODING HUMAN A ERYTHROPOIETIN ANALOG

[75] Inventors: Gregory F. Okasinski, Wadsworth; Peter J. DeVries, Des Plaines; Berry S. Mellovitz, Chicago; Joseph L. Meuth; Verlyn G. Schaefer, both of Libertyville, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 537,754

[22] PCT Filed: Apr. 29, 1994

[86] PCT No.: PCT/US94/04755

§ 371 Date: Oct. 23, 1995

§ 102(e) Date: Oct. 23, 1995

[87] PCT Pub. No.: WO94/25055

PCT Pub. Date: Nov. 10, 1994

Related U.S. Application Data

[63] Continuation-in-part of Ser. No. 055,076, Apr. 29, 1993, abandoned.

[51] Int. Cl.$^6$ ............... C12N 15/19; C12N 15/63; C12N 15/10; C07K 14/505

[52] U.S. Cl. ............... 435/69.5; 435/320.1; 435/325; 514/2; 530/350; 530/397; 530/399; 536/23.51

[58] Field of Search ............... 530/397, 350, 530/395, 399; 536/23.51; 435/240.2, 320.1, 172.1, 69.4; 514/8, 2

[56] References Cited

U.S. PATENT DOCUMENTS 4,835,260  5/1989  Shoemaker ............... 530/397

OTHER PUBLICATIONS

McDonald, J.D. et al. Molecular and Cellular Biology 6 : 842–848, (1986).
Nagao, M. et al. Biochemica et Biophysica Acta 1171 : 92–102, (1992).
Boissel, J.P. et al. *The Biology Of Hematopoieis*, Wiley-Liss, New York; pp. 227–232 (1990).
Rudinger, J. *Peptide Hormones*, University Park Press, Baltimore; pp. 1–7 (1976).
Relny et al. (1987) J. BIOL. CHEM. 262 : 17156–17163.

*Primary Examiner*—Lila Feisee
*Assistant Examiner*—Michael Pak
*Attorney, Agent, or Firm*—Andreas M. Danckers

[57] ABSTRACT

Analogs of human erythropoietin, including the [$X^{33}$, $Cys^{139}$, des-$Arg^{166}$] and [$Cys^{139}$, des-$Arg^{166}$] analogs, as well as methods for making and using such analogs and pharmaceutical compositions containing the same.

27 Claims, 4 Drawing Sheets

DNA ENCODING HUMAN A ERYTHROPOIETIN ANALOG

This application is a continuation-in-part of U.S. patent application Ser. No. 08/055,076, filed on Apr. 29, 1993 now abandoned.

TECHNICAL FIELD

The present invention relates to analogs of human erythropoietin, a glycoprotein known to be useful in inducing erythropoiesis and in treating conditions, such as anemia, which are due to low erythrocyte or reticulocyte count. The invention also relates to methods and compositions for making the analogs and methods of using the analogs to induce erythropoiesis and treat conditions, such as anemia, which result from inadequate erythrocyte or reticulocyte count.

BACKGROUND OF THE INVENTION

Erythropoietin is a naturally-occurring glycoprotein hormone with a molecular weight that was first reported to be approximately 39,000 daltons (T. Miyaki et al., *J. Biol. Chem.* 252:5558–5564 (1977)). The mature hormone is 166 amino acids long and the "prepro" form of the hormone, with its leader peptide, is 193 amino acids long (F. Lin, U.S. Pat. No. 4,703,008). The mature hormone has a molecular weight, calculated from its amino acid sequence, of 18,399 daltons (K. Jacobs et al., *Nature* 313:806–810 (1985); J. K. Browne et al., *Cold Spring Harbor Symp. Quant. Biol.* 51:693–702 (1986)).

Structural characterization of human urinary erythropoietin has identified a des-Arg166 form that results from specific removal of the Arg residue at the carboxy-terminus of the mature protein (M. A. Recny et al., *J. Biol. Chem.* 262:17156–17163 (1987)). Recny et al., supra, propose that the physiologically active form of erythropoietin circulating in human plasma is the des-Arg166 form.

Human erythropoietin contains three N-linked carbohydrate chains (H. Sasaki et al., *J. Biol. Chem.* 262:12059–12076 (1987); E. Tsuda et al., Biochemistry 27:5646–5654 (1988); and M. Takeuchiet al., *J. Biol. Chem.* 263:3657–3663 (1988)). The carbohydrate content of erythropoietin is similar in both naturally-occurring urinary erythropoietin and in hormone produced by expression, in mammalian cells in culture, of a cloned DNA which has been transfected into the cells and which encodes the prepro form of the hormone. The N-linked glycosylation sites are located at amino acid residues 24, 38, and 83. Both urinary and recombinant erythropoietin also contain a single O-linked glycosylation site at amino acid residue 126 (H. Sasaki et al., supra; E. Tsuda et al., supra; M. Takeuchi et al., supra; and M. Goto et al., *Biotechnology* 6:67–71 (1988)). The carbohydrate content of erythropoietin is a complex fucosylated tetra antennary type chain with and without N-acetyllactoseamine repeating units (M. Takeuchi et al., supra) and contributes approximately 40% of the mass of erythropoietin.

Human erythropoietin is primarily produced as a glycoprotein hormone by the adult kidney (H. P. Koeffler and E. Goldwasser, *Ann. Intern. Med.* 97:44–47 (1981)). The cells that produce erythropoietin in the kidney are rare and are located in the inner cortex of the renal parenchyma in the intersticium between renal tubules (S. T. Koury et al., *Blood* 71:524–528 (1988), and C. Lacombe et al., *J. Clin. Invest.* 81:620–623 (1988)). Consequently, destruction of kidney tissue, as occurs in renal failure, results in decreased production of erythropoietin and a concomitant reduction in erythrocyte count and anemia.

While fetal liver cells in vitro can produce erythropoietin (A. Kurtz et al., *Endocrinology* 118:567–572 (1986)), no compensating erythropoietin production occurs in most end-stage renal failure patients, and serum erythropoietin levels are normally restored only after successful renal transplantation (W. F. Denny et al., *J. Lab. Clin. Med.* 67:386 (1966)).

Late stage erythropoiesis, in most cases, is accomplished by a single glycosylated hormone, erythropoietin, produced in a single tissue. A rare alternate route of erythropoiesis has been documented in a human anephric patient with a high hematocrit. The isolated erythrotropic factor in this patient has been shown to be human insulin-like growth factor 1, or IGF-I (A. Brox et al., *Exp. Hematol.* 17:769–773 (1989), and L. F. Congote et al., *J. Clin. Endocrin. Metab.* 72:727–729). IGF-I is undoubtedly the human counterpart of the bovine erythrotropic factor described as having both in vivo and in vitro activity by L. F. Congote (*Biochem. Biophys. Res. Comm.* 115:477–483 (1983)). IGF-I receptors are known to exist on human erythrocytes, and these receptors could allow this rare alternate route of late stage erythropoiesis to occur via interaction of IGF-I and its specific receptor (T. Izami et al., *J. Clin. Endocrinol. Metab.* 62:1206–1212 (1986), and C. D. Costigan et al., *Clin. Invest, Med.* 11:4751 (1988)). However, the nucleotide sequence of the erythropoietin receptor gene is known and shows no sequence homology to that of the human IGF-I receptor (A. D. D'Andrea et al., *Cell* 57:277–285 (1989)), indicating that the alternate route of erythropoiesis via IGF-I is unrelated to the erythropoietin-mediated pathway of late stage erythropoiesis.

While no other alternate routes of late stage erythropoiesis are known, several factors have been described that can potentiate the action of erythropoietin. Late stage erythropoiesis is dependent on erythropoietin but is influenced by testosterone, estrogens, and erythroid-potentiating factor, while the early stage of erythropoiesis is dependent on burst-promoting activity in addition to erythropoietin (N. N. Iscove in Hematopoietic Cell Differentiation, eds. D. W. Golde, M. J. Cline and C. F. Fox [Academic Press, New York] pp. 37–52). Factors such as IL-3, granulocyte macrophage colony-stimulating factor and interleukin-9 are known to have burst-forming activity. However, it is unclear whether these activities have any physiological role in erythropoiesis (J. Suda et al., *Blood* 67:1002–1006 (1986); C. A. Sieff et al., *Science* 230:1171–1173 (1985); and R. E. Donahoe et al., *Blood* 75:2271–2275 (1989). Recently, a factor termed "erythroid differentiation factor" has been shown to potentiate the activity of erythropoietin in vivo and in vitro (H. E. Broxmeyer et al., *Proc. Natl. Acad. Sci.* 85:9052–9056 (1988); J. Yu et al., *Nature* 330:765–767 (1987)). This factor has been shown to be identical to activin A (follicle-stimulating hormone-releasing protein) and to be inhibited by follistatin, a specific inhibitor of activin A; however, the physiological role of activin A remains to be determined (M. Shiozaki et al., *Proc. Natl. Acad. Sci.* 89:1553–1556 (1992)). Thus, after nearly twenty years of investigation, there is no clear indication that erythropoiesis is controlled by any hormone other than erythropoietin.

In the absence of any alternative hormones which affect erythropoiesis, several attempts to both probe erythropoietin structure and significantly improve the characteristics of erythropoietin by site-directed mutagenesis have appeared in the literature. The molecular cloning of the human gene encoding erythropoietin reveals a DNA sequence coding for a preprohormone of 193 amino acids and a mature hormone of 166 amino acids. The availability of cloned DNA encoding the hormone and its precursor (i.e., the prepro form) provides the opportunity for mutagenesis by standard methods in molecular biology. See U.S. Pat. No. 4,703,008, supra.

The first mutant erythropoietins (i.e., erythropoietin analogs), prepared by making amino acid substitutions and deletions, have demonstrated reduced or unimproved activity. As described in U.S. Pat. No. 4,703,008, replacement of the tyrosine residues at positions 15, 49 and 145 with phenylalanine residues, replacement of the cysteine residue at position 7 with an histidine, substitution of the proline at position 2 with an asparagine, deletion of residues 2–6, deletion of residues 163–166, and deletion of residues 27–55 does not result in an apparent increase in biological activity. The $Cys^7$-to-$His^7$ mutation eliminates biological activity. A series of mutant erythropoietins with a single amino acid substitution at asparagine residues 24, 38 or 83 show severely reduced activity (substitution at position 24) or exhibit rapid intracellular degradation and apparent lack of secretion (substitution at residue 38 or 183). Elimination of the 0-linked glycosylation site at Serine126 results in rapid degradation or lack of secretion of the erythropoietin analog (S. Dube et al., *J. Biol. Chem.* 33:17516–17521 (1988)). These authors conclude that glycosylation sites at residues 38, 83 and 126 are required for proper secretion and that glycosylation sites located at residues 24 and 38 may be involved in the biological activity of mature erythropoietin.

The suggestion that glycosylation of erythropoietin is required for in vitro biological activity is contrary to reports showing that deglycosylatjed erythropoietin is fully active in vitro bioassays (M. S. Dordal et al., Endocrinology 116: 2293–2299 (1985); J. K. Browne et al., *Cold Spring Harbor Symp. Quan. Biol.* 51:693–702 (1986); U.S. Pat. No. 4,703, 008; E. Tsuda et al., *Eur. J. Biochem.* 188:405–411 (1990); and K. Yamaguchi, et al., *J. Biol. Chem.* 266:20434–20439 (1991)). A set of analogs of erythropoietins, similar to those studied by Dube et al., supra, has been constructed using oligonucleotide-directed mutagenesis to probe the role of glycosylation sites in the biosynthesis and biological activity of erythropoietin (K. Yamaguchi et al., supra). These investigators conclude that glycosylation is important for the correct biosynthesis and secretion of erythropoietin but has no affect on the in vitro activity of the molecule. However, all of the mutant erythropoietins studied by Yamaguchi et al., which involve changes at the glycosylation sites, lack in vivo biological activity.

Glycosylation of erythropoietin is widely accepted to play a critical role in the in vivo activity of the hormone (P. H. Lowy et al., *Nature* 185:102–105 (1960); E. Goldwasser and C. K. H. Kung, *Ann. N.Y. Acad. Science* 149:49–53 (1968); W. A. Lukowsky and R. H. Painter, *Can. J. Biochem.* 50:909–917 (1972); D. W. Briggs et al., *Amer. J. Phys.* 201:1385–1388 (1974); J. C. Schooley, *Exp. Hematol.* 13:994–998; N. Imai et al., *Eur. J. Biochem.* 194:457–462 (1990); M. S. Dordal et al., *Endocrinology* 1 16:2293–2299 (1985); E. Tsuda et al., *Eur. J. Biochem.* 188:405–411 (1990); U.S. Pat. No. 4,703,008; J. K. Brown et al., *Cold Spring Harbor Symposia on Quant. Biol.* 51:693–702 (1986); and K. Yamaguchi et al., *J. Biol. Chem.* 266:20434–20439 (1991)).

The lack of in vivo biological activity of deglycosylated analogs of erythropoietin is attributed to a rapid clearance of the deglycosylated hormone from the circulation of treated animals. This view is supported by direct comparison of the plasma half-life of glycosylated and deglycosylated erythropoietin (J. C. Spivak and B. B. Hoyans, *Blood* 73:90–99 (1989), and M. N. Fukuda, et al., *Blood* 73:84–89 (1989).

Oligonucleotide-directed mutagenesis of erythropoietin glycosylation sites has effectively probed the function of glycosylation but has failed, as yet, to provide insight into an effective strategy for significantly improving the characteristics of the hormone for therapeutic applications.

A series of single amino acid substitution or deletion mutants have been constructed, involving amino acid residues 15, 24, 49, 76, 78, 83, 143, 145, 160, 161, 162, 163, 164, 165 and 166. In these mutants are altered the carboxy terminus, the glycosylation sites, and the tyrosine residues of erythropoietin. The mutants have been administered to animals while monitoring hemoglobin, hematocrit and reticulocyte levels (European Published Patent Application No. 0 409 113). While many of these mutants retain in vivo biological activity, none show a significant increase in their ability to raise hemoglobin, hematocrit or reticulocyte (the immediate precursor of an erythrocyte) levels when compared to native erythropoietin.

Another set of mutants has been constructed to probe the function of residues 99–119 (domain 1) and residues 111–129 (domain 2) (Y. Chern et al., *Eur. J. Biochem.* 202:225–230 (1991)). The domain 1 mutants are rapidly degraded and inactive in an in vitro bioassay while the domain 2 mutants, at best, retain in vitro activity. These mutants also show no enhanced in vivo biological activity as compared to wild-type, human erythropoietin. These authors conclude that residues 99–119 play a critical role in the structure of erythropoietin.

The human erythropoietin molecule contains two disulfide bridges, one linking the cysteine residues at positions 7 and 161, and a second connecting cysteines at positions 29 and 33 (P.-H. Lai et al., *J. Biol. Chem.* 261:3116–3121 (1986)). Oligonucleotide-directed mutagenesis has been used to probe the function of the disulfide bridge linking cysteines 29 and 33 in human erythropoietin. The cysteine at position 33 has been converted to a proline residue, which, mimics the structure of murine erythropoietin at this residue. The resulting mutant has greatly reduced in vitro activity. The loss of activity is so severe that the authors conclude that the disulfide bridge between residues 29 and 33 is essential for erythropoietin function (F.-K. Lin, Molecular and Cellular Aspects of Erythropoietin and Erythropoiesis, pp. 23–36, ed. I. N. Rich, Springer-Verlag, Berlin (1987)).

Site-specific oligonucleotide-directed mutagenesis of the methionine residue at position 54 of human erythropoietin results in a molecule which retains the in vivo biological activity of the parent (wild-type) molecule with the added advantage of providing an erythropoietin preparation which is less susceptible to oxidation (Shoemaker, U.S. Pat. No. 4,835,260).

A large number of mutants of the human erythropoietin gene have been described in several scientific publications and patent applications. These mutants have spanned the entire length of the molecule, have produced partially- or completely-deglycosylated molecules, have altered the structures of the disulfide bridges in the molecule, and have attempted to improve the therapeutic activity of the molecule. Of all such attempts to alter erythropoietin, none have succeeded in producing a molecule with enhanced in vivo biological activity or other improved properties for therapeutic applications.

The failure to identify a naturally-occurring alternate route of late stage erythropoiesis and the heretofore unsuccessful attempts to produce an erythropoietin analog with enhanced in vivo activity have provided little insight into how an improved erythrotropic molecule could be made.

SUMMARY OF THE INVENTION

It has now been discovered that substitution of cysteine for the arginine at position 139 of human erythropoietin and analogs thereof, including those wherein the cysteine at position 33 is replaced with another amino acid, results in a glycohormone which is significantly improved in in vivo erythropoietic activity and in its potential for use in therapeutic applications, such as induction of erythropoiesis and treatment of anemia.

Further, it has been found unexpectedly that a first analog of a mammalian and especially human erythropoietin, which has significantly reduced, or even no, in vitro or in vivo biological activity as a result of a change in amino acid sequence (at a first position) from that of the naturally occurring, wild-type protein, can be converted to a significantly more active second analog by an additional, compensating change in amino acid sequence (at a second position) from that of the wild-type protein. This result is obtained even though the second position is distant, in the primary sequence of the protein, from the first position. Indeed, it has been found that such a second analog can have in vivo or in vitro activity which is nearly the same as, or even greater than, that of the wild-type erythropoietin. In this context, by "distant" is intended a separation of at least 1 amino acid position, more typically at least about 10 amino acid positions, and possibly even more than 100 amino acid positions. It is readily possible to identify such double mutants, in which a change in amino acid at one position compensates for, or even overcomes, the reduction in activity due to a change in an amino acid at another, distant position.

Also discovered and disclosed for the first time are methods and compositions for making the improved erythropoietin analogs of the invention by expression, in mammalian cells, of DNA sequences which encode a prepro form of the analogs, i.e., analogs having appended at their amino-terminus a leader peptide of a mammalian erythropoietin. Many of the analogs of the invention are, surprisingly, substantially more active in erythropoiesis than native erythropoietin when administered to an anemic or non-anemic mammal and have the additional, surprising and significant advantage of requiring less frequent administration than native erythropoietin to achieve a predetermined therapeutic effect.

The analogs of mammalian (and especially human) erythropoietin of the invention retain immunological characteristics or in vitro biological activity similar to that of the corresponding, native erythropoietin, so that concentrations of the analogs in blood, culture media, pharmaceutical preparations and the like can readily be measured and monitored by conventional means employed with the native glycohormone.

BRIEF DESCRIPTION OF THE DRAWINGS

The present invention is described in connection with the attached drawings, in which.

DETAILED DESCRIPTION OF THE INVENTION

Figure 1:
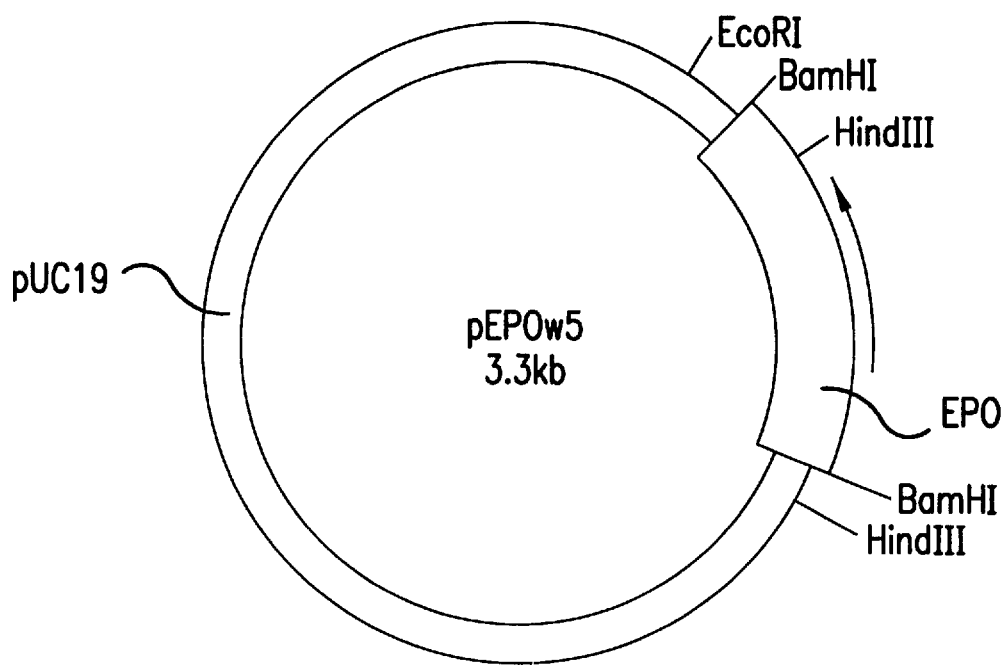
FIG. 1 is a schematic representation of the plasmid pEPOw5, the construction of which is described in Example 1.

In one of its aspects, the present invention is an analog of human erythropoietin which has the arginine residue at position 139 of the native glycohortmone replaced with a cysteine residue.

In another of its aspects, the present invention is a further-modified analog wherein the cysteine residue at position 33 of wild-type erythropoietin is replaced with any one of the other 19 naturally-occurring amino acids, preferably proline.

In each instance, preferred examples of the analogs of the invention are those which lack the arginine residue at position 166 (i.e., which are des-$Arg^{166}$).

In another of its aspects, the present invention is a double-stranded DNA sequence which comprises a segment of 498 or 495 nucleotides encoding an erythropoietin analog of the invention.

In a further aspect, the present invention entails a double-stranded DNA sequence comprising two, contiguous subsegments wherein a first subsegment is the above segment of 498 or 495 nucleotides and the other subsegment encodes the leader peptide of a mammalian preproerythropoietin, and wherein the two subsegments are joined such that, in the single polypeptide encoded by the contiguous subsegments, the carboxy-terminus of the leader peptide is adjacent the amino-terminus of the erythropoietin analog. Preferred leader peptides are those of mouse, monkey, hamster and human preproerythropoietin, and most preferred is the human leader peptide. The amino acid sequences of the human and monkey leader peptides are given in SEQ ID NO:6 and SEQ ID NO:7, below.

In a still further aspect, the invention entails a double-stranded DNA sequence which is an eukaryotic expression vector for expression, in a mammalian cell in culture, of a preproerythropoietin analog of the invention. Any mammalian cell can be employed for this purpose, but CHO (Chinese hamster ovary) cells are preferred. As understood in the art, such an expression vector is made by ligating a cDNA sequence that encodes the analog of interest into a position in the vector where the cDNA will be transcribed, along with signals required for translation of the transcript, when the vector is in a cell (e.g., a mammalian cell) which provides the proteins and other components necessary to recognize the signals on the vector to initiate transcription and the signals on RNA transcribed from the vector (including a segment corresponding to the inserted cDNA) to effect translation and production of the polypeptide coded for by the cDNA. Positioning a cDNA "operably for expression" in an expression vector means positioning it so that RNA can be transcribed from the vector and ultimately translated in the cell transformed with the vector to make the protein encoded by the cDNA.

The invention also entails mammalian cells in culture which comprise an eukaryotic expression vector for expression, in said cell, of a cDNA encoding a preproerythropoietin analog of the invention. Such expression leads to secretion into the culture medium of mature, glycosylated analog.

The present invention further encompasses a method of using a mammalian cell which comprises an eukaryotic expression vector suitable for expression, in said cell, of a DNA sequence which consists of two contiguous segments which together encode a precursor polypeptide. This precursor polypeptide consists of a leader peptide of a mammalian preproerythropoietin joined at its carboxy-terminus to the amino-terminus of an human erythropoietin analog. Accordingly, one of said segments encodes said leader peptide, while the other of said segments has 498 or 495 base pairs and encodes an erythropoietin analog of the invention. The above method comprises culturing said cell in a culture medium under conditions whereby said cell secretes said erythropoietin analog into the culture medium. The analog can then be isolated from the culture medium, purified and formulated into a pharmaceutically composition for administration to a mammal, preferably an human.

The invention also encompasses a second analog of human erythropoietin which has specific activity in erythropoiesis that is significantly greater than that of a first analog, which first analog has specific activity in erythropoiesis that is significantly less than that of native, human erythropoietin. This second analog is one having the same number and sequence of amino acids as native human erythropoietin except at a first and a second position in said sequence, where said second analog has amino acids that are different from those at the same positions in the sequence of native human erythropoietin, while said first analog is one having the same number and sequence of amino acids as said second analog except at either said first or said second position, where in the first analog the amino acid is the same as that found in the sequence of native human erythropoietin. The discovery of these "second analogs" of the invention rests on our discovery that a compensating change in amino acid sequence can be made which restores at least some activity lost due to the presence, in a "first analog", of an amino acid which is different from the amino acid found at the corresponding position in the native glycoprotein. It is anticipated that, in some instances, the second analog will be more active (i.e., have greater in vivo specific activity in stimulating erythropoiesis) than the native glycohormone, while the first analog will be inactive in vivo.

The present invention also provides a process for making such a second analog of erythropoietin, described in the preceding paragraph, which process comprises (a) preparing a library of eukaryotic expression vectors, each of which comprises a cDNA sequence, positioned operably for expression in a mammalian cell, which (i) encodes a double mutant of native human preproerythropoietin (i.e., a mutant with changes in amino acids at two positions from those present in the native glycohormone), (ii) comprises the triplet (codon) coding for the non-native amino acid of a first analog of native human erythropoietin, which first analog has no substantial activity in stimulating erythropoiesis, has the same number of amino acids as native human erythropoietin, but has at one position in its sequence an amino acid that differs from that found in the corresponding position in native human erythropoietin, and (iii) comprises a random mutation in a segment of cDNA which does not code for any part of the leader peptide of the native preproerythropoietin and does not include said triplet coding for said non-native amino acid of said first analog; (b) transfecting the library of expression vectors into mammalian cells for expression; and (c) selecting cells which secrete the desired second analog.

The present invention also provides a method for using such a second, double-mutant analog, with activity enhanced in comparison with a first, single-mutant analog of diminished activity relative to the native glycohormone, to make a third analog which has greater in vivo activity in stimulating erythropoiesis than the second analog. This process comprises changing the amino acid in said second analog, which is found in said first analog but not in native human erythropoietin, to the amino acid present at the corresponding position in native human erythropoietin.

The present invention further entails an analog of human erythropoietin which has the same number and sequence of amino acids as native human erythropoietin, except for a difference in amino acid at one position in said sequence, and which has greater activity in erythropoiesis than native human erythropoietin, said analog made by the process just described, i.e., by using a second analog which itself has in vivo specific activity in stimulating erythropoiesis which is at least as great as that of the native glycohormone.

The present invention also entails pharmaceutical compositions useful for inducing erythropoiesis and/or treating anemia in a mammal (preferably a human) which comprise a therapeutically effective amount of an analog of human erythropoietin of the invention in combination with a pharmaceutically acceptable carrier. Such pharmaceutical compositions, like analogs of the invention, are to be administered under the guidance of a physician or veterinarian and in such amounts or concentrations as are effective in inducing the needed amount of erythropoiesis. The carrier to be employed may be any physiologically tolerated vehicle, including but not limited to a buffer, salt, stabilizer, preservative or other adjuvant, combined with the glycohormone in a form suitable for administration by injection (usually intravenously or subcutaneously) or otherwise.

Administration will be in accordance with a dosage regimen that will be readily ascertained by the skilled, based on in vivo specific activity of the analog in comparison with human erythropoietin and based on what is now known in the art concerning the administration of human erythropoietin for inducing erythropoiesis and treating various conditions, such as anemia, in humans, including anemia in patients suffering from renal failure. Dosage of an analog of the invention may vary somewhat from individual to individual, depending on the particular analog and its specific in vivo activity, the route of administration, the medical condition, age, weight or sex of the patient, the patient's sensitivities to the analog or components of vehicle, and other factors which the attending physician will be capable of readily taking into account. With regard to therapeutic uses of analogs of the invention, reference is made to U.S. Pat. Nos. 4,703,008 and 4,835,260; see also the chapter on (recombinant) [des-Arg$^{166}$]human erythropoietin at pages 591–595 of the Physicians' Desk Reference, 46th Edition (Medical Economics Data, Montvale, N.J. (1992)). Commercially available preparations of recombinant [des-Arg$^{166}$] human erythropoietin have 2,000, 3,000, 4,000 or 10,000 units of the glycohormone per ml in preservative-free aqueous solution with 2.5 mg/ml human serum albumin, 5.8 mg/ml sodium citrate, 5.8 mg/ml NaCl, and 0.06 mg/ml citric acid, pH 6.9 (+/−0.3).

Reference herein to erythropoietin, unless otherwise qualified, is to the "mature" human protein, absent the leader peptide and the arginine at position 166.

"Preproerythropoietin" means the protein including the leader peptide and Arg$^{166}$ prior to processing, upon expression in a mammalian cell of a cDNA encoding the preproform, to glycosylate and. ultimately, secrete the mature protein into the culture medium. The amino acid sequences of the native human protein and the native human preproprotein are given in SEQ ID NO:1.

The terms "native" and "wild-type", as used herein, are intended to be synonymous.

Standard abbreviations, as follows, are used herein for the 20 "naturally occurring" amino acids:

| | |
|---|---|
| L-alanine | Ala |
| L-arginine | Arg |
| L-asparagine | Asn |
| L-aspartic acid | Asp |
| L-cysteine | Cys |
| L-glutamic acid | Glu |
| L-glutamine | Gln |
| glycine | Gly |
| L-histidine | His |
| L-isoleucine | Ile |
| L-leucine | Leu |
| L-lysine | Lys |
| L-methionine | Met |
| L-phenylalanine | Phe |
| L-proline | Pro |
| L-serine | Ser |
| L-threonine | Thr |
| L-tryptophan | Trp |
| L-tyrosine | Tyr |
| L-valine | Val |

The standard, one-letter codes "A", "C", "G" and "T" are used herein to represent the nucleotides adenylate, cytidylate, guanylate and thymidylate, respectively. Those skilled in the art will understand that, in DNA sequences, the nucleotides are 2'-deoxyribonucleotide-5'-phosphates (or, at the 5'-end, triphosphates) while, in RNA sequences, the nucleotides are ribonucleotide-5'-phosphates (or, at the 5'-end, triphosphates) and uridylate (U) occurs in place of T. By "N" is meant any one of the four nucleotides.

A reference herein to an analog protein, "Protein X", as "[$X^a$, $Y^b$, des-$Z^c$]Protein X" means the analog in which the amino acid at position a in a native Protein X has been replaced with amino acid X, the amino acid at position b in the native Protein X has been replaced with amino acid Y, and the amino acid Z, normally present at position c in native Protein X, is missing.

As used herein, "SV2dhfrSVdeltaSJneo([X',Yb]hEPO)" means the expression vector SV2dhfrSVdeltaSJneoEPO with the cDNA coding for preproerythropoietin (see SEQ ID NO:1) replaced with a cDNA such that cultured mammalian cells transfected with the vector will secrete the [$X^a$, $Y^b$] analog of mature erythropoietin.

The invention is illustrated in more detail in the following examples, which are not intended to be limiting.

Further detail in connection with carrying out various procedures described herein, such as cloning, insertion of a cDNA operably for expression into an expression vector, transfection of eukaryotic or mammalian expression vectors into mammalian cells and selection of transfected cells, culturing of mammalian cells to obtain desired heterologous protein by secretion into the culture media, sequencing of DNAs, carrying out nucleic acid amplification with polymerase-chain-reaction (PCR), synthesis of primers for carrying out such amplification, protein or nucleic acid purification techniques, and the like, as well as further examples of such things as mammalian expression vectors, cell lines suitable for use in expression from such vectors, culture media for culturing transfected cell lines, leader peptides for mammalian preproerythropoietins other than human and monkey, nucleic acid amplification methods, and the like, are readily available and known in the art. See, for example, Current Protocols in Molecular Biology, eds. F.M. Ausubel et al., Wiley Interscience, John Wiley and Sons, Inc., New York (1993) through Supplement 21; the ATCC Catalogue of Cell Lines and Hybridomas, 7th Ed., American Type Culture Collection, Rockville, Md., USA (1992); and the ATCC Media Handbook, American Type Culture Collection, Rockville, Md. (1984).

EXAMPLE 1

Preparation of Plasmid Expression Vector SV2dhfrSVdeltaSJneo

A. Construction of a Synthetic Gene Encoding Human Erythropoietin.

A DNA encoding full-length, human preproerythropoietin was made using standard phosphoramidite chemistry to prepare 8 double-stranded oligonucleotides having the sequences of SEQ ID NOS:8–15 and then applying the Fok-1 gene synthesis method, described by Mandecki and Bolling in Gene 68:101–108 (1988), using the 8 oligonucleotides. The oligos of sequences SEQ ID NOS:8–14 were each ligated into the SmaI site of pWM500, the construction of which is described in Mandecki and Bolling, supra, and then cloned in that vector. The oligo of sequence SEQ ID NO:15 was ligated into the Smal site of pWM501, the construction of which also is described in Mandecki and Bolling, supra, and then cloned in that vector. Each oligo, after the cloning, was obtained by digestion of the vector with Fok-1 and purification of the oligo by electro-elution from a polyacrylamide gel. The 8 oligos were then ligated to one another to provide a 640 base pair ("bp") polynucleotide, which comprised a 625 bp BamHI fragment, with an intended sequence that would be the same as that of SEQ ID NO:1 which, in turn, comprised a segment encoding the preproerythropoietin. The 640 bp fragment was designed to have an HindIII site on the 5'-end and a unique EcoRI site on the 3'-end for ease of subsequent subcloning. After the ligation to provide the 640 bp fragment, that fragment was digested with EcoRI and partially digested with HindIII, and the resulting 640 bp fragment was ligated into similarly digested pUC19 to give plasmid pEPOw5, which is illustrated in FIG. 1. The sequence of the 640 bp fragment in pEPOw5 was determined to attempt to verify that the preproerythropoietinencoding fragment would in fact encode human preproerythropoietin.

B. Correction of Synthesis Mistakes by Oligonucleotide-directed Mutagenesis.

The preproerythropoietin-encoding fragment of pEPOw5 contained two nucleotide errors, which resulted in amino acids changes at residues eighty-four and ninety-five from the amino acids present at those positions in human erythropoietin. To correct the errors, so that the amino acids at positions 84 and 95 would be the same as in human erythropoietin, required changing a C present at position 352 of SEQ ID NO:1 to a T; changing a T present at position 353 to a C; changing a C present at position 385 to a G; and changing an A present at position 387 to a G. Thus, pEPOw5 was digested with EcoRI to completion and with HindIII to partial completion. The digested plasmid was electrophoresed in a 0.7% agarose gel and a fragment of about 640 bp was electroeluted from the agarose into a 7.5M ammonium acetate salt bridge using a model UEA electroeluter (International Biotechnologies Inc., New Haven, Conn., USA) for one hour at 100 volts. The replicative form of M13mp18 was digested to completion with HindIII and EcoRI and ligated to the eluted fragment. The ligated DNAs were transfected into *E. coli* (strain DH5alpha F') and the phage plaques were transferred to 2× YT media. Phage were propagated preparatively in *E. coli* DH5alpha F' cells. Phage were titred on *E. coli* CJ236 cells [dut-1, ung-1] and uracil containing phage prepared from the same strain by infection at a M.O.I. of 0.2 as recommended by the manufacturer of the MutaGene mutagenesis kit (Bio-Rad Laboratories, Richmond, Calif., USA). Template DNA was extracted from the phage as recommended by the manufacturer. Mutagenesis of residues eighty-four and ninety-five was specified by simultaneous annealing of phosphorylated oligonucleotide-1, with the sequence of SEQ ID NO:2, and oligonucleotide-2, with the sequence of SEQ ID NO:3, to template DNA. DNA with the appropriate sequence corrections was synthesized in vitro as recommended by the manufacturer of the mutagenesis kit. The mutated (corrected) DNA was transfected into DH5alphaF' cells and phage plaques were isolated for DNA sequencing. After sequence confirmation, the mutated (sequence-corrected) preproerythropoietin-encoding DNA fragment was subcloned for expression as described below. The DNA sequence of the synthetic human preproerythropoietin-encoding DNA is shown in SEQ ID NO:1.

C. Construction by Oligonucleotide-directed Mutagenesis of DNA encoding prepro-pm25

Construction, by oligonucleotide-directed mutagenesis, of DNA that encodes prepro-pm25 (i.e., [Pro$^{33}$, Cys$^{139}$] human preproerythropoietin) was achieved by the methods described above to provide the corrected native, human preproerythropoietin-encoding DNA. The corrected preproerythropoietin-encoding DNA was used as the source of template DNA to provide prepro-pm25-encoding DNA. The DNA mutagenesis primers were (i) oligonucleotide-3, having the sequence specified in SEQ ID NO:4, which changed the nucleotides at both positions 199 and 200 in SEQ ID NO:1 to C's, and (ii) oligonucleotide-4, having the sequence specified in SEQ ID NO:5, which changed the nucleotide at position 517 in SEQ ID NO:1 to a T.

D. Subcloning of Preproerythropoietin-encoding and prepro-pm25-encoding DNA into an Eukaryotic Expression Vector The eukaryotic expression vector, SV2dhfrSVdeltaSJneo, was digested with XbaI for 2 hours and the DNA was extracted with an equal volume of buffer saturated phenol/chloroform (1:1) followed by chloroform extraction. The digested DNA was ethanol-precipitated, dried and resuspended in 50 microliters of TE (10 mM Tris, pH 8.0, 10 mM EDTA). The digested vector was treated with calf alkaline phosphatase for one hour at 37° C. The phosphatased vector was extracted with phenol:chloroform and chloroform, dried and resuspended in REact2 buffer (50 mM Tris-HCl, pH 8.0, 10 mM MgCl2, 50 mM NaCl) (Gibco-BRL, Gaithersburg, Md., USA). The protruding 5'-ends of the XbaI-digested vector were blunted by a filling reaction with the large fragment of DNA polymerase 1 (Klenow) and 0.1 mM 2'-deoxyribonucleoside triphosphates for thirty minutes at room temperature. The Klenow fragment was removed by phenol/chloroform extraction and the DNA was ethanol-precipitated and resuspended in TE (50 microliters).

Figure 2:
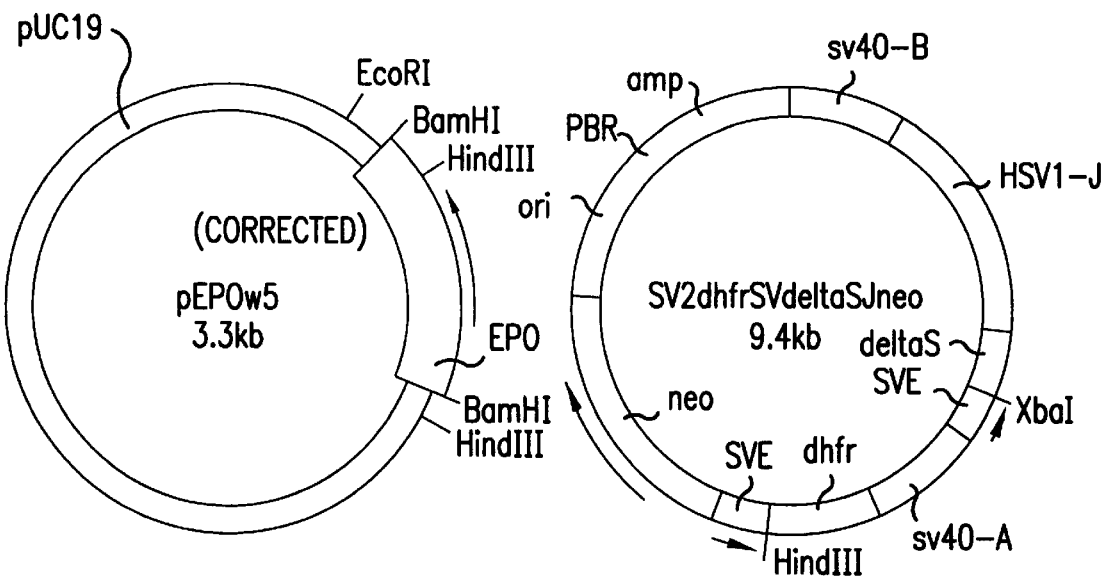
FIG. 2 is a schematic representation of the process, described in Example 1 and used to make, from plasmid pEPOw5(corrected) and plasmid SV2dhfrSVdeltaSJneo, the expression vector SV2dhfrSVdeltaSJneoEPO, which can be used to transform mammalian cells in culture to make native human erythropoietin.
Figure 2:
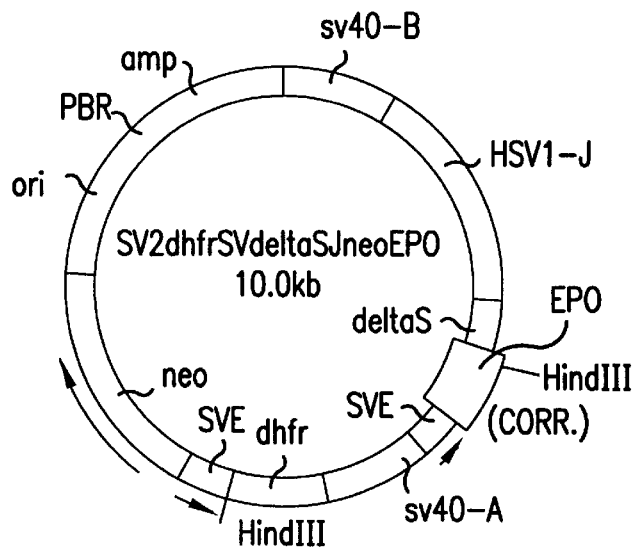

The DNA fragments encoding human preproerythropoietin and prepro-pm25 were subcloned into the XbaI-digested and Klenow-blunted expression vector as BamHI fragments, which also were blunted. The fragments were propagated as part of plasmids in *E. coli* strain HB-101. Purified plasmid was prepared from 1-liter cultures by lysis with SDS at pH 8.0 and subsequent cesium chloride density gradient centrifugation (T. Maniatis et al., Molecular Cloning, pp 89–94, Cold Spring Harbor Press, Cold Spring Harbor, N.Y., 1982). Plasmid DNA concentration was determined by absorbance at 260 nm. Preparative quantities were digested with BamHI and electrophoresed in a 0.7% agarose gel in Tris-acetate buffer. A band of approximately 625 bp was electro-eluted from the agarose into a 7.5M ammonium acetate salt bridge using a model UEA electroeluter (International Technologies Inc.) for one hour at 100 volts. The eluted DNA was ethanol-precipitated and resuspended in TE. The 5'-protruding ends were made blunt by enzymatic repair as described above for the expression vector. The blunted expression vector and the fragments were ligated with T4 DNA ligase at 15° C. for 16 hours. The ligated mixture was transformed into *E. coli* and the correct clone identified by standard methods. The clones were propagated at the one-liter stage and plasmid DNA was prepared by lysis with sodium dodecyl sulfate (SDS) and cesium chloride density gradient centrifugation as described above. The plasmids (expression vectors) were stored in TE at 4° C. The expression vector for the human preproerythropoietin was designated SV2dhfrSVdeltaSJneoEPO, and that for the [Pro$^{33}$, Cys$^{139}$] human preproerythropoietin was designated SV2dhfrSVdeltaSJneopm25. A schematic representation of the construction and subcloning of SV2dhfrSVdeltaSJneoEPO is illustrated in FIG. 2.

SV2dhfrSVdeltaSJneo was constructed by addition of a neomycin resistance gene expression cassette and the SVdeltaSJ expression cassette to the publicly-available plasmid, pSV2-dhfr (American Type Culture Collection, Rockville, Md., USA, Accession No. 37146; Berg et al., *Mol. Cell. Biol.* 1:854–864 (1981)). Plasmid pSV2-dhfr has a 2.3 kilobase pair (kbp) PvuII-to-EcoRI fragment (designated "ori PBR amp" in FIG. 2), which was derived from pBR322 and has the bacterial origin of replication ("ori") and the beta-lactamase gene (which provides ampicillin resistance) ("amp") from plasmid pBR322. Plasmid pSV2-dhfr also has a 1.9 kbp expression cassette, which has a 0.34 kbp PvuII-to-HindIII fragment of simian virus 40 (SV40) DNA with the T-antigen promoter (designated "SVE" in FIG. 2), a 0.74 kbp HindIII-to-BglII fragment with a cDNA sequence encoding mouse dihydrofolate reductase (designated "dhfr" in FIG. 2), and a 1.6 kbp BglII-to-EcoRI fragment of SV40 DNA including a 0.82 kbp BglII-to-BamHI fragment having the SV40 T-antigen mRNA splicing and polyadenylation signals (designated "sv40-A" in FIG. 2) and a 0.75 kbp BamHI-to-EcoRI fragment having no known function (designated "sv40-B" in FIG. 2). The neomycin resistance gene expression cassette (to provide neomycin resistance to cells transformed with the vector) was inserted at the PvuII site of plasmid pSV2-dhfr by routine subcloning methods (e.g., Maniatis et al., supra). The neomycin resistance gene expression cassette is a 1.8 kbp fragment containing a 0.25 kbp PvuII-to-SmaI fragment of Herpes simplex virus-1 ("HSV1") DNA with the thymidine kinase promoter, a 1.0 kbp BglII-to-SmaI fragment of transposon Tn5 encoding the enzyme providing neomycin resistance, and a 0.6 kbp SmaI-to-PvuII fragment of HSV1 DNA encoding the thymidine kinase mRNA polyadenylation site and signal; all of these fragments are readily available to skilled practitioners of the art. The SVdeltaSJ expression casette is a 2.5 kbp fragment with the 0.34 kbp PvuII-to- HindIII fragment of SV40 DNA with the T-antigen promoter ("SVE" in FIG. 2), an XbaI site for insertion of an heterologous DNA to be expressed under control of the SV40 T-antigen promoter, a 0.44 kbp HpaI-to-BamHI fragment of hepatitis B virus (subtype adw) DNA with a 3'-enhancer from the hepatitis B virus surface antigen gene (designated "delta S" in the Figure), and a 1.85 kbp BamHI to PvuII fragment of HSV1 DNA from the BamHI J fragment of that DNA. The SVdeltaSJ cassette was preassembled and inserted into the BamHI site (after blunting with Klenow) of SV2-dhfr. Insertion of the neomycin resistance gene expression cassette and the SVdeltaSJ expression cassette into plasmid pSV2-dhfr resulted in the plasmid expression vector SV2dhfrSVdeltaSJneo, shown in FIG. 2.

EXAMPLE 2

Alternative Construction of a Synthetic Gene Encoding pm25

In an alternative procedure for preparing the above SV2dhfrSVdeltaSJneopm25 expresion vector, DNA encoding full-length pm25 is synthesized de novo by using standard phosphoramidite chemistry. A series of double stranded oligonucleotides are prepared in a manner similar to that described in Example 1; however, unlike the approach of Example 1, the oligonucleotides when assembled form a gene already containing mutations in the native erythropoietin sequence, as for example changes encoding a proline residue at position 33 and a cysteine residue at position 139. The synthetic oligonucleotides are assembled using the Fok-1 gene synthesis method of Mandecki and Bolling, supra, or by other methods known to those skilled in the art of gene synthesis. The sequence of the resulting synthetic pm25 gene is confirmed by standard DNA sequencing of the assembled prepro-pm25 gene.

The assembled prepro-pm25 gene is then subcloned into a plasmid vehicle/expression vector by the standard methods previously described, such as by inclusion of unique restriction sites at the 5' and 3' ends of the synthetic prepro-pm25 gene and by subsequent restriction endonuclease digestion and subcloning.

EXAMPLE 3

Alternative Construction of a Prepro-pm25 Gene by Mutagenic RT-PCR

Prepro-erythropoietin analog genes may also be prepared using reverse transcription-polymerase chain reaction. Representative of such a procedure is the preparation of a prepro-pm25-encoding DNA sequence, in which mammalian cells are treated in culture with 100 uM cobalt chloride for 48 hours in a manner known to enhance the level of expression of the gene encoding native erythropoietin (H. Scholz et al., *Am. J. Physiol.* 263:474–479 (1992)). The cells are then washed with cold saline solution and are harvested from culture by centrifugation. The cell pellet is lysed by resuspension in saline containing 1% Triton X-100 and centrifuged to remove nuclei, with the resulting supernate containing total mRNA. Alternatively, the cell pellet can be lysed with guanidine isothiocyanate to prepare total RNA.

mRNA is then isolated by annealing to Dynabeads Oligo dt 25 (deoxythymidine) oligonucleotide-bearing beads as recommended by the manufacturer (Dynal A/S, N-0212 Oslo, Norway). Total RNA is prepared from guanidine isothiocyanate-lysed cells by standard methods. Complimentary DNA is synthesized from Oligo dt-selected mRNA isolated from approximately $10^5$ cells or from approximately 0.1 $\mu$g of total RNA using random hexamer primers and reverse transcriptase. The cDNA serves as template for a mutagenic polymerase chain reaction. The PCR reaction is carried out using three sets of primers, and the prepro-pm25 gene is synthesized as three distinct fragments (amino, middle and carboxy) with one set of primers for each fragment.

The 5' primer of the amino fragment contains restriction sites for subsequent molecular manipulations and sequences complimentary to the 5' end of the cDNA template. The 3' primer of the amino fragment contains a restriction site for molecular manipulation and sequences complimentary to the cDNA template.

The 5' primer of the middle fragment contains a restriction site capable of annealing the 3' restriction site of the amino fragment, a codon encoding the proline residue at position 33 of prepro-pm25, and sequences complimentary to the cDNA template. The 3' primer of the middle fragment contains a codon encoding a cysteine residue at position 139 of prepro-pm25, a restriction site for subsequent molecular manipulation, and sequences complimentary to the cDNA template.

The 5' primer of the carboxy fragment contains a restriction site capable of annealing to the 3' restriction site of the 3' primer of the middle fragment and sequences complimentary to the cDNA template. The 3' primer of the carboxy fragment contains sequences complimentary to the cDNA template and a restriction site for subsequent manipulations.

Each individual fragment can be subcloned and sequence confirmed prior to final assembly of the entire prepro-pm25 gene. The prepro-pm25 gene is assembled by restriction endonuclease digestion of the fragments using the restriction sites incorporated into each of the primers and ligation of the resulting complimentary ends. The assembled prepro-pm25 gene contains 5' untranslated and 3' untranslated sequences originally found in the message encoding erythropoietin as well as coding sequences of the prepro-pm25 gene. These untranslated sequences can be removed using subsequent PCR reactions with primers complimentary to the coding sequences of the prepro-pm25 gene, using methods known to those skilled in the art. The entire gene encoding prepro-pm25 is then subcloned into a suitable expression vector as previously described.

EXAMPLE 4

Expression of Proteins by Transformed Cell Lines

A. Transfection of Dihydrofolate Reductase Deficient Chinese Hamster Ovary Cells Each of the plasmids SV2dhfrSVdeltaSJneoEPO and SV2dhfrSVdeltaSJneopm25 were transfected into CHO/dhfrcells[dxb-111] (Uriacio et al., *Proc. Nat. Acad. Sci.* 77:4461–4466 (1980); American Type Culture Collection Accession No. CRL 9096), which are readily available to one skilled in the art, using the cationic liposome-mediated procedure (P. L. Felgner, et al., *Proc. Natl. Acad. Sci.* 84:7413–7414 (1987)). Similar transfections were done with an expression plasmid expressing the hepatitis B virus surface antigen and the resulting transfected cells served as a source of negative control culture fluid for the in vivo bio-assay experiments described below. CHO/dhfr- cells were cultured in Ham's F-12 media supplemented with 10% fetal calf serum, L-glutarnine (1 $\mu$M) and freshly seeded into a 25 cm2 flask at a density of 5–8×$10^5$ cells per flask twenty four hours prior to transfection. Ten micrograms of plasmid DNA was added to 1.5 mls of Opti-MEM I reduced serum media with 2.4 g/L sodium bicarbonate (Gibco-BRL), and 100 microliters of Lipofectin Reagent (Gibco-BRL) for liposome-mediated transfection of DNA into cells in tissue culture was added to a second 1.5 ml portion of Opti-MEM I media. These two solutions were prepared in polystyrene tubes. The two solutions were mixed and incubated at room temperature for 20 minutes. The culture medium was removed from cells and replaced with the Opti-MEM I-Lipofectin-DNA solution. The cells were incubated for three hours at 37° C. after which the Opti-MEM I-Lipofectin-DNA solution was replaced with culture medium for an additional 24 hours prior to selection.

B. Selection and Amplification

One day after transfection, cells were passaged 1:3 and incubated with dhfr/G418 selection medium (hereafter, "F-12 minus medium G"). Selection medium was Ham's F-12 with L-glutamine and without hypoxanthine, thymidine or glycine (Gibco-BRL), supplemented with dialyzed fetal calf serum (JRH Biosciences, Lenexa, Kans., USA) and 300 micrograms per ml G418 (Gibco-BRL).

Colonies showing the presence of dihydrofolate reductase (Ringold et al., *J. Mol. Appl. Genet.* 1:165–174 (1981)) plus aminoglycoside phosphotransferase (P. J. Southern and P. Berg, *J. Mol. Appl. Genet.* 1:327–341 (1981)) appeared after 4–5 days of incubation of transfected cells with F-12 minus medium G. After approximately two weeks, DHFR/G418 cells were sufficiently expanded to allow passage and continuous maintenance in F-12 minus medium G.

Amplification of the transfected erythropoietin or pm25 genes was achieved by stepwise selection of DHFR+, G418+ cells with methotrexate (reviewed by R. Schimke, *Cell* 37:705–713 (1984)). Cells were incubated with F-12 minus medium G, containing 150 nM methotrexate (MTX), for approximately two weeks until resistant colonies appeared. The MTX resistant cells were passaged and maintained in the appropriate selection medium. Further amplification was achieved by selection with 5 μM MTX, and cells were continuously maintained in the appropriate selection medium.

C. Maintenance and Storage of Cell Lines

Cells in culture and undergoing various selection or amplification procedures were re-fed with the appropriate culture medium three times weekly. Cells were passaged 1:5, with appropriate medium, into 75 cm² flasks using standard methods. Cryostorage was by resuspension of 2–4×10⁶ cells in 1.8 ml of the appropriate culture medium containing 5% DMSO (Sigma, SL Louis, Mo., USA) and cold storage for 24 hours at −80° C. and then permanent storage at −135° C.

D. Production of Erythropoietin and pm25 in Serum Free Medium

Cells transfected with either the erythropoietin- (i.e., rEPO-) or the pm25-expressing DNA were grown to confluence in F-12 minus medium G containing 300 micrograms/ml G418, then the culture media was removed and replaced with production medium (5 ml/25 cm² of surface area). Production medium was VAS medium (serum-free culture medium supplemented with fish protamine sulfate) with L-glutamine, HEPES buffer, and with out phenol red (JRH Biosciences). Cells were cultured at 37° C. for three days and the conditioned medium was used as a source of rEPO or pm25.

Both the rEPO and the pm25 polypeptides obtained from the conditioned medium were des-Arg$^{166}$.

EXAMPLE 5

In Vitro Biological Activity of Expressed Proteins

A. In Vitro Bioassay

Erythropoietin activity was determined by radiolabelled thymidine incorporation into spleen cells of phenylhydrazine-treated mice (G. Krystal, *Exp. Hematol.* 11:649–660 (1983)). Female C57/6 mice, at least ten weeks old, were injected intraperitoneally (ip) twice with phenylhydrazine (60mg/kg) 72 and 96 hours prior to cervical dislocation. The largest spleens were removed and gently teased into alpha MEM culture media (without nucleotides) supplemented with 0.2% bovine serum albumin (BSA). The tissue suspension was incubated for one minute in a 50 ml polypropylene tube and the spleen cells were removed from large tissue aggregates. Spleen cells were centrifuged for 10 minutes at 1,500 rpm in a clinical centrifuge and resuspended in spleen culture media (SCM). SCM is alpha MEM (without nucleotides) containing antibiotics, 0.4% BSA, 2.0% Nutridoma NS (Boehringer Mannheim Biochemicals, Indianapolis, Ind., USA), 30% fetal calf serum (Hyclone, Logan. Utah) selected for erythroid cell growth, and 0.1 mM 2-mercaptoethanol. The cell suspension was passed through a nylon mesh (200) to remove remaining aggregates; then nucleated cells were counted in a hemacytometer. Cells were incubated in SCM at room temperature for approximately three hours at 8×10⁶ cells/ml with occasional stirring. Fifty microliter aliquots of the cell suspension were inoculated into wells of U-shaped 96-well microtiter plates to which an equal volume of sample, in SCM, was added. The cells were incubated at 37° C. in a $CO_2$ incubator (5% $CO_2$) for 22–24 hours, then 0.6 μCi of tritiated thymidine was added to each well and incubation continued for an additional two hours. Reactions were terminated by placing the microtiter plates on ice. Cells were harvested onto glass fiber discs using a PHD cell harvester (Cambridge Technology, Watertown, Mass., USA), washed at least ten times with distilled water and once with 95% ethanol. Radioactivity was measured with a scintillation counter (Beckman Instruments, Fullerton, Calif., USA). Native, human, non-recombinant erythropoietin (Toyobo New York, Inc., New York, N.Y., USA) (hEPO) was included as a positive control in all assays at 0.25–16 milliunits/well. Each data point was the average of triplicate determinations from at least three wells/sample.

Figure 3:
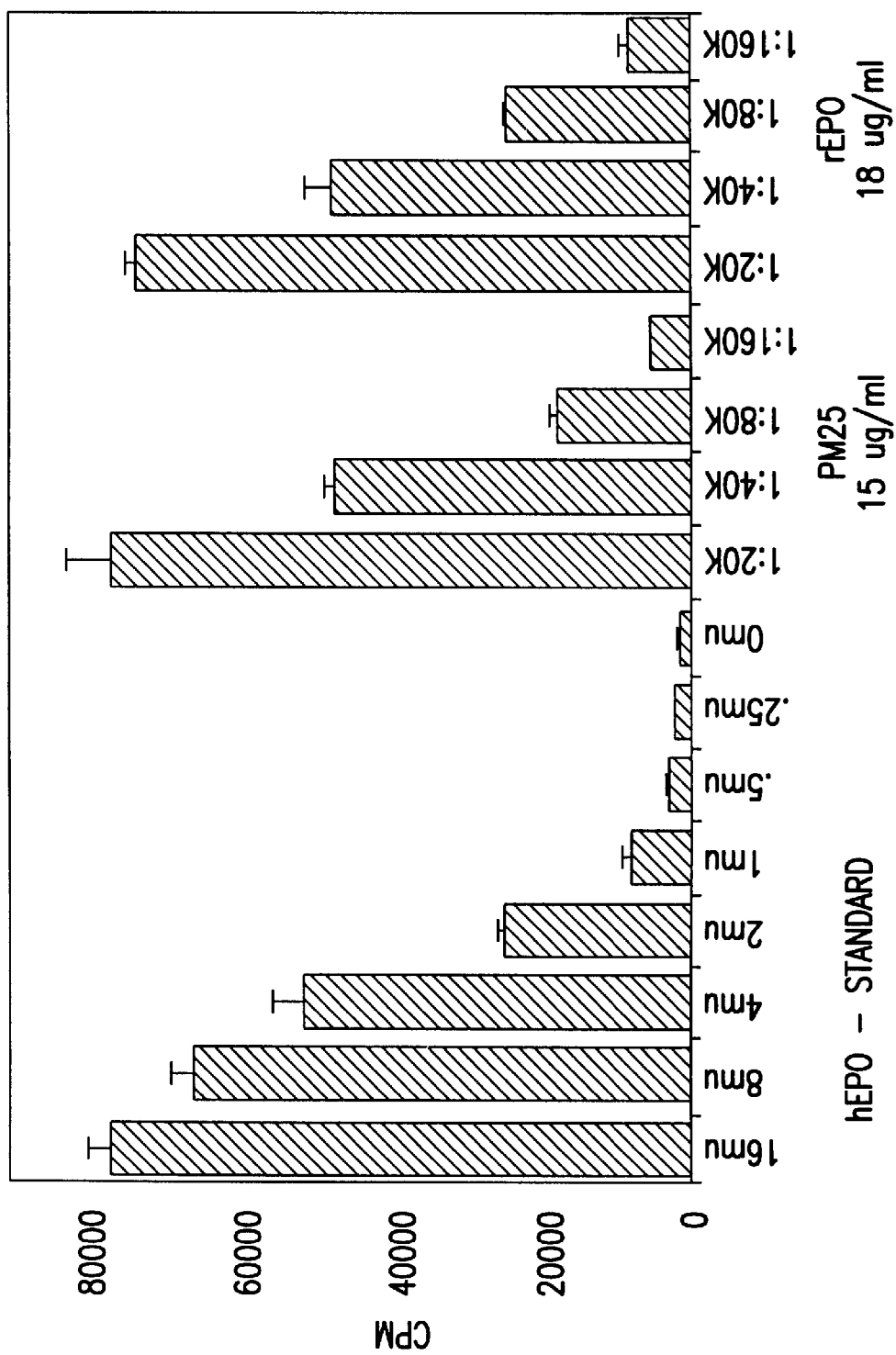
FIG. 3 is a graph illustrating the activities of native, "non-recombinant" human erythropoietin (hEPO Standard), native, "recombinant" human erythropoietin produced in culture by dhfr- Chinese hamster ovary cells which have been transformed with expression vector SV2dhfrSVdeltaSJneoEPO (rEPO), and the "recombinant" human erythropoietin analog pm25 with proline at residue 33 and cysteine at residue 139 (pm25), produced in culture by dhfr- Chinese hamster ovary cells which have been transformed with an analog of expression vector SV2dhfrSVdeltaSJneoEPO which includes DNA encoding the prepro form of such analog rather than the prepro form of native human erythropoietin.

As shown in FIG. 3, a dose-dependent response was obtained when hEPO (i.e., erythropoietin standard), rEPO (i.e., recombinant native erythropoietin obtained from CHO cells transfected with SV2dhfrSVdeltaSJneoEPO) and pm25 were assayed. The data in FIG. 3 depict results from an assay of purified pm25 and rEPO over a series of dilutions, beginning at 15 μg/ml for pm25 and 18 μg/ml for rEPO. These data clearly demonstrate that the mutant erythropoietin, pm25 ([Pro$^{33}$, Cys$^{139}$]human erythropoietin) has in vitro activity equal to human erythropoietin even though pm25 does not have a cysteine residue at position 33 and therefore cannot form a disulfide bond between residues 29 and 33, which prior workers have believed to be essential for erythropoietic activity.

B. Radioimmunoassay and In Vitro Specific Activity

The masses of rEPO and pm25 were determined using a commercial radioimmunoassay kit (Incstar, Stillwater, Minn., USA) as described by the manufacturer, with the exception of inclusion of hEPO as a positive control for generating a standard curve. rEPO was purified to homogeneity as described below and the mass was determined by amino acid composition analysis. Standard hydrolysis was done using approximately 50–300 picomoles of protein under vacuum for 2 hours at 155° C. using a Pico Tag Work station (Waters, Milford, Mass., USA). The purified standard was stored at −80° C. and a fresh aliquot used for the standard curve of each radioimmunoassay. The purified standard generated a linear response (log concentration vs. counts) when used at concentrations ranging from 0.25–2.0 ng/ml. At 2 ng/ml of standard, approximately 1050 counts were observed; at 1 ng/ml, approximately 2000 counts were observed; at 0.5 ng/ml, approximately 3200 counts were observed; and at 0.25 ng/ml, approximately 4250 counts were observed. Thus, the in vitro specific activity of both the rEPO or pm25 from culture supernates of transfected CHO cells was routinely calculated and ranged from 90,000 to 130,000 units/mg.

EXAMPLE 6

In Vivo Biological Activity of Expressed Proteins

A. Wheat Germ Agglutinin Chromatography

Conditioned production media from cells transfected with each of rEPO, pm25 and HbSAg (as a negative control) were passed through a wheat germ agglutinin-Sepharose column to partially purify (approximately tenfold) and concentrate the erythropoietic activity. Thirty milliliters of conditioned medium was passed through a disposable minicolumn (Spectrum Medical Industries, Inc., Houston, Tex., USA), containing one milliliter of wheat germ agglutinin-Sepharose (Sigma) previously equilibrated with phosphate-buffered saline (PBS). The flowthrough was collected and passed through the column a second time, then the column was washed with nine column volumes of PBS and erythropoietic activity eluted with 1.5 column volumes of N,N-diacetylchitibiose (J. L. Spivak et al., *Blood* 52:1178–1188 (1978). The eluted material was stored at −80° C. until use in an in vivo bio-assay. The in vitro activity of the rEPO or pm25 from the wheat germ agglutinin chromatography was indistinguishable from the values obtained from conditioned production medium.

B. Starved Rat In Vivo Bioassay of rEPO and pm25

The in vivo activities of rEPO and pm25 were determined in a modified starved rat bioassay (W. Fried et al., *Proc. Soc. Exp. Med.* 94:237–241 (1957). In this assay. reticulocyte cell counts were monitored rather than incorporation of radio-active iron. Groups of four or five animals were treated with rEPO or pm25, each of which had been partially purified by wheat germ agglutinin chromatography as described above. Negative control animals were treated with wheat germ eluate prepared from conditioned production medium from HbSAg transfected cells. In a typical assay, rats were fasted from Monday through Friday and were injected with rEPO or pm25 intravenously on Tuesday, Wednesday and Thursday. Reticulocyte counts were determined (see below) on Monday and Tuesday and the average of the two taken as the starting reticulocyte count. Reticulocyte counts were determined on Friday and the percent reticulocytes remaining calculated for each animal, and the average for each group calculated. Negative control rats routinely retained approximately 50% of their starting reticulocytes. The results for rats treated with either rEPO or pm25 are expressed as the ratio of the average treated group to the negative control; rats treated with 60 or 100 ngs of rEPO or pm25 showed a dose-dependent increase in reticulocytes (see Table 1).

TABLE 1

In Vivo Bio-Assay Results

| Sample | Treatment | % Reticulocytes | Treated/Control |
|---|---|---|---|
| Mock | T, W, Th | 53 | — |
| EPO | 60 ng T, W, Th | 81 | 1.54 |
| EPO | 100 ng T, W, Th | 102 | 1.94 |
| pm25 | 60 ng T, W, Th | 108 | 2.05 |
| pm25 | 100 ng T, W, Th | 132 | 2.50 |

Rats treated with equivalent doses (as determined by radioimmunoassay) of pm25 show a dose-dependent response which is significantly greater than that seen with rEPO. Rats were also treated with pm25 or rEPO at equivalent doses determined by in vitro units. Animals treated with pm25 showed an improved response when compared to the animals treated with equivalent doses of rEPO (see Table 2).

TABLE 2

In Vivo Bio-Assay Results

| Sample | Treatment | % Reticulocytes | Treated/Control |
|---|---|---|---|
| Mock | T, W, Th | 36 | — |
| EPO | 1.75 u T, W, Th | 75 | 2.08 |
| EPO | 5.25 u T, W, Th | 89 | 2.45 |
| EPO | 8.75 u T, W, Th | 116 | 3.20 |
| pm25 | 1.75 u T, W, Th | 85 | 2.35 |
| pm25 | 5.25 u T, W, Th | 119 | 3.29 |
| pm25 | 8.75 u T, W, Th | 133 | 3.66 |

The increased potency of pm25 was also evident in animals treated with a single dose of pm25. Rats treated with a single dose of pm25 administered on a Tuesday showed a response substantially equivalent to that of rats treated with three doses of rEPO (see Table 3).

TABLE 3

In Vivo Bio-Assay Results

| Sample | Treatment | % Reticulocytes | Treated/Control |
|---|---|---|---|
| Mock | T, W, Th | 54 | — |
| EPO | 20 ng T, W, Th | 78 | 1.45 |
| EPO | 60 ng T, W, Th | 80 | 1.48 |
| EPO | 100 ng T, W, Th | 106 | 1.97 |
| pm25 | 100 ng T only | 92 | 1.71 |

Rats treated with a single dose of rEPO on Tuesday, Wednesday or Thursday, when compared to animals treated with three doses of rEPO (one on each day), showed no such equivalence (see Table 4).

TABLE 4

In Vivo Bio-Assay Results

| Sample | Treatment | % Reticulocytes | Treated/Control |
|---|---|---|---|
| Mock | T, W, Th | 38 | — |
| EPO | 20 ng T, W, Th | 69 | 1.83 |
| EPO | 60 ng T, W, Th | 80 | 2.11 |
| EPO | 100 ng T, W, Th | 106 | 2.78 |
| EPO | 100 ng T only | 59 | 1.55 |
| EPO | 100 ng W only | 62 | 1.64 |
| EPO | 100 ng Th only | 56 | 1.46 |

These data show that pm25 both has increased in vivo potency and also is an effective erythrotropic agent upon single-dose administration (i.e., is effective without multiple dosings).

C. Flow Cytometric Determination of Reticulocytes

Reticulocyte counts were determined by flow cytometric analysis of peripheral blood reticulocytes using thiazole orange staining (L. G. Lee et al., *Cytometry* 7:508–517 (1986). Heparinized rat whole blood was prepared for flow cytometry using Retic-COUNT® thiazole orange stain (Becton Dickinson, San Jose, Calif., USA) as recommended by the manufacturer. Each five microliter sample of blood was mixed with 1 ml of thiazole orange stain and incubated in the dark at room temperature for 45 minutes. Unstained controls were prepared in a similar manner but lacked thiazole orange and contained PBS. Analysis was completed within 90 minutes after the staining incubation since prolonged staining gave abnormally high values.

Samples were analyzed with an EPICS ELITE flow cytometer (Coulter Electronics, Hialeah, Fla., USA) equipped with an argon ion laser at 488 nm and 15 MW of power. Log forward angle light scatter, log side scatter (90 degrees), and log green fluorescence parameters were collected. Standard ELITE filters were used; neutral density 1 for forward light scatter, 488 dichroic long pass for side scatter, and 525 band pass for green fluorescence.

The flow cytometer was aligned daily using Immuno-Check fluorospheres (Coulter Electronics) and standardized using Immuno-Brite Level II fluorospheres (Coulter Electronics). Standardization compensated for the day-to-day variation in instrument settings. A computer protocol was established to collect three histograms; dual-parameter log side scatter vs. log forward scatter, log fluorescence vs. log forward scatter, and single-parameter log green fluorescence.

A stained sample was analyzed to establish gates for inclusion of only erythroid cells. An amorphous gate was drawn around a population containing lymphoid and erythroid cells on the log forward scatter vs. log side scatter plot, which eliminated platelets and background debris. This gated population was then represented on a log fluorescence vs. log forward scatter histogram. A rectangular gate was drawn around the negative erythroid population and the positively staining reticulocyte population, but excluding the highly staining lymphoid population. The gated erythroid population was represented on a single-parameter log green fluorescence histogram. An unstained control sample was analyzed on the instrument and 25,000 events were collected. The cursor was placed to include 0.1% of the autofluorescing cells and the stained samples were analyzed. Reticulocytes were expressed as a percentage of all erythroid cells.

EXAMPLE 7

Purification of Expressed Proteins

A. Purification of rEPO

Proteing rEPO was purified from conditioned production media by a combination of ion-exchange, wheat germ lectin, and reverse phase chromatography. Typically, ten liters of conditioned medium were clarified by centrifugation and then concentrated ten-fold using a Benchmark rotary concentrator (Membrex, Garfield, N.J., USA) with a 10,000-dalton molecular weight cut-off membrane at 4° C. The concentrated harvest was centrifuged at 15,000×g for thirty minutes, then diluted with an equal volume of cold distilled water containing 25 KIU (kilo international units) of aprotinin per milliliter, after which the pH was adjusted to 7.3–7.4, if necessary. The diluted concentrate was passed over two ion-exchange columns connected in series. The first column was an S-Sepharose Fast Flow resin (Pharmacia-LKB, Inc., Piscattaway, N.J., USA) and the second a DEAE Sepharose Fast Flow resin (Pharmacia-LKB). The columns were each 1.6×33 cm and were equilibrated with 20 mM $NaH_2PO_4$, pH 7.4, 20 mM NaCl. Under these conditions, rEPO did not bind to either column; however, a substantial purification was achieved since many other proteins did bind. The flow-through and a 200 ml wash were loaded onto a 20 ml wheat germ agglutinin-Sepharose column (Sigma) previously equilibrated with 20 mM $NaH_2PO_4$, pH 7.4, 20 mM NaCl and washed exhaustively with buffer containing 135 mM NaCl. rEPO was eluted with wash buffer containing 10 mM N,N,-diacetylchitibiose (J. L. Spivac et al., supra). Fractions (3.5 ml) were collected, each was adjusted to contain 25 KIU aprotinin per milliliter, and the rEPO of each was examined by SDS-PAGE (sodium dodecyl sulfate-polyacrylamide gel electrophoresis) (U. K. Laemmli, *Nature* 227:680–685 (1970); H. Schagger and G. von Jagow, *Anal. Biochem.* 166:368–379 (1987).

Fractions which contained the highest levels of rEPO as determined by Coomassie Blue[3] staining were pooled, acidified with 5% TFA (trifluoroacetic acid) (30 μl/ml) and chromatographed on a POROS R2/H column (2.1×100 mm) (a reverse phase column, PerSeptive Biosystems, Cambridge, Mass., USA). The equilibration buffer was 0.1% TFA in 5% $CH_3CN$ and the elution buffer was 0.08% TFA in 80% $CH_3CN$. Six minutes after loading, a fifteen minute gradient elution (from 0% to 100% buffer) was performed. Fractions were manually collected and purity was assayed by SDS-PAGE. rEPO was stored at −80° C.

On SDS-PAGE, rEPO migrated between 31,000- and 43,000-dalton markers and had an apparent molecular weight of 36,000 daltons. Subsequent digestion with the protease Lys-C and amino acid sequence analysis (see below) confirmed the presence of rEPO and revealed no other protein.

B. Purification of pm25

Protein pm25, obtained from conditioned production media, was purified by an identical procedure to that described for rEPO. Unlike rEPO, however, SDS-PAGE electrophoresis of the purified pm25 revealed the presence of a high molecular protein or proteins with an electrophoretic mobility of approximately 60,000 daltons that co-purified with pm25. Because of this high molecular weight contaminant, an altered purification procedure was implemented to separate the high molecular weight component from pm25. After the previously-described wheat germ agglutinin-Sepharose chromatography step, the eluted material was acidified with 10% TFA in 5% $CH_3CN$ (100 μl/ml). The sample was chromatographed on the SMART[3] high performance liquid chromatography system (Pharmacia), automated to collect product-containing fractions by monitoring absorbance, using a Pharmacia URPC C2/C18 column (2.1×100 mm) and a flow rate of 200 microliters per minute. The initial buffer was 0.1% TFA in 5% $CH_3CN$ and the elution buffer was 0.08% TFA in 80% $CH_3CN$. Five minutes after loading, the concentration of the elution buffer was increased from 0% to 40% in one minute. A thirty minute gradient from 40% to 70% of the elution buffer was performed to elute pm25. Fractions were collected using the SMART system "peak detection" capability and SDS-PAGE was used to identify pm25. The partially-purified pm25 was taken to dryness and redissolved in 100 mM $CH_3CO_2NH_4$, pH4.1, 6M urea. The sample was loaded onto a Mono-S cation exchange column (Pharmacia) (1.6×50 mm), equilibrated in the same buffer, and chromatographed at room temperature using a SMART system. The sample was loaded at 100 microliters per minute and chromatographed at 150 microliters per minute. Five minutes after loading, a twenty minute gradient from 0–50% eluting buffer (100 mM $CH_3CO_2NH_4$, pH4.1, 1M NaCl, 6M urea) was performed. Fractions were collected using the SMART system "peak detection" capability and SDS-PAGE was used to identify pm25. Eluted pm25 was then re-chromatographed on a URPC C2/C18 column (2.1×100 mm) as described above. The sample was acidified with 5% TFA and loaded onto the column at 200 microliters per minute. Initial buffer was 0.1% TFA in 5% $CH_3CN$ and the elution buffer was 0.08% TFA in 80% $CH_3CN$. Five minutes after loading, a 25 minute gradient elution (from 0 to 100% buffer) was performed. The SMART system "peak detection" capability was used to collect fractions and SDS-PAGE performed to locate and assess purity. Electrophoretic analysis revealed a single band migrating between the 29,000 and 43,000 dalton markers with an apparent molecular weight of approximately 36,000 daltons. Subsequent protease digestion with Lys-C and sequence analysis revealed the presence of pm25 and no other proteins.

EXAMPLE 8

Biological Activity of Purified Proteins

A. In Vivo Activity of rEPO and pm25 in a Non-Anemic Rat Model

The biological activities of purified rEPO and pm25 were compared in a long-term, non-anemic rat model by measuring hematocrits of treated and mock-treated rats. Groups of five rats were treated three times per week with rEPO or pm25 or were mock-treated with vehicle (PBS containing 0.2% BSA) for a total of four weeks. Four groups of animals were treated by intravenous injection with 150, 300, 450 or 600 ngs of rEPO in vehicle and two groups treated in the same way with 150 or 300 ngs of pm25 in vehicle. One group of animals served as controls and were treated intravenously with vehicle three times per week for four weeks. Hematocrits were determined for each animal at the end of the four week period and the average hematocrit values were calculated for each group. The animals treated with 150 ngs of pm25 showed a response substantially equivalent to that of animals treated with 300 ngs of rEPO. Similarly, animals treated with 300 ngs of pm25 showed a response substantially equivalent to that of animals dosed with 600 ngs of rEPO. In this long-term model, therefore, pm25 was approximately twice as effective in raising the hematocrit of treated animals as native recombinant erythropoietin (see Table 5).

TABLE 5

Long-term In Vivo Bio-Assay Results

| Sample | Treatment | Hematocrit (Final) |
|---|---|---|
| Mock | M, W, F | 52.3 |
| EPO | 150 ng M, W, F | 53.3 |
| EPO | 300 ng M, W, F | 58.0 |
| EPO | 450 ng M, W, F | 60.2 |
| EPO | 600 ng M, W, F | 62.6 |
| pm25 | 150 ng M, W, F | 58.3 |
| pm25 | 300 ng M, W, F | 65.8 |

In a similar experiment, single weekly dosing of pm25 was compared to three doses per week of rEPO. One group of animals was treated with 300 ngs of rEPO three times per week for four weeks. Two groups of animals were treated with either 450 or 600 ngs of pm25 once per week. One group of animals was treated with vehicle three times per week and served as mock-treated controls. At the end of the four-week treatment schedule, hematocrits were determined for each animal and the average hematocrit value for each group was calculated. Animals treated once per week with pm25 showed a response substantially equivalent to animals treated with 300 ngs of rEPO three times per week. These data demonstrate that pm25 offers the advantage of reduced frequency of dosing when compared to erythropoietin (see Table 6).

TABLE 6

Long-term In Vivo Bio-Assay Results

| Sample | Treatment | Hematocrit (Final) |
|---|---|---|
| Mock | M, W, F | 52.8 |
| EPO | 300 ng M, W, F | 58.4 |
| pm25 | 450 ng W only | 56.2 |
| pm25 | 600 ng W only | 58.8 |

In yet another related experiment, single weekly dosing of rEPO was tested by administering rEPO once per week in a long-term, non-anemic rat model and comparing hematocrits of mock-treated and rEPO-treated animals. Groups of five animals were mock-treated with vehicle (PBS containing 0.2% BSA), treated with rEPO three times per week, or treated with rEPO once weekly for a total of four weeks. One group of animals was treated with vehicle alone three times per week for four weeks and served as the vehicle control. Three groups of animals were treated with 150, 300 or 450 ngs of rEPO in vehicle three times per week for four weeks. Three additional groups of animals were treated with 300, 600 or 900 ngs of rEPO in vehicle once weekly for four weeks.

The animals treated three times weekly showed a dose-dependent increase in hematocrit levels ranging from 55.3% to 60.8% (see Table 7). Animals treated with rEPO at 300 or 600 ngs once per week showed no appreciable increase in hematocrit compared to the vehicle treated controls; however, animals treated with 900 ngs once weekly showed only a modest increase in hematocrit as compared to vehicle-treated animals and a significantly lower increase than that found in animals treated with the lowest dose of rEPO administered three times per week. These data, when compared to those obtained with once-weekly administration of pm25 as shown in Table 6, suggest that the analogs of the present invention produce greater in vivo erythropoietic effects upon once-weekly dosing than native erythropoietin.

TABLE 7

Long-term In Vivo Bio-Assay Results

| Sample | Treatment | Hematocrit (Final) |
|---|---|---|
| Mock | 3 times weekly (TIW) | 51.0 |
| EPO | 150 ng TIW | 55.3 |
| EPO | 300 ng TIW | 57.0 |
| EPO | 450 ng TIW | 60.8 |
| EPO | 300 ng once weekly (QW) | 51.3 |
| EPO | 600 ng QW | 50.5 |
| EPO | 900 ng QW | 53.0 |

B. In Vivo Activity of rEPO and pm25 in a Non-Anemic Cynomolgus Monkey Model

The biological activities of purified rEPO and pm25 were compared in a long term non-anemic Cynomolgus monkey model by measuring hematocrits and hemoglobin concentrations in Cynomolgus monkeys treated three times per week with rEPO or once per week with pm25. Male animals were divided into two groups of five. Hematocrits and hemoglobin concentrations were determined three times during the week prior to treatment by removing 0.5 ml of blood for each determination at 48 hour intervals. The average of the three determinations for each group was used as the pretreatment value for each group of animals.

One group of animals was treated with 2 μg/kg rEPO three times per week for a total of four weeks. A second group of animals was treated with 4 μg/kg pm25 once per week for a total of four weeks. Treatment with erythropoietin is known to deplete circulating iron and efficacy of the drug can be limited by available iron (J. Eschbach et al., *New Eng. J. of Med.* 316:73–78 (1987)); consequently, both treatment groups of Cynomolgus monkeys were treated with 10 mg peptonized iron (Rogenic, Forest Pharmaceuticals, St. Louis, Mo., USA) twice per week to eliminate any iron deficiency that might result from or limit the efficacy of rEPO or pm25.

At the end of the treatment period, hematocrits and hemoglobin concentrations were measured twice at 72 hour intervals. The final hematocrits and hemoglobin concentrations were calculated as the average of these values; it was found that hematocrit and hemoglobin values for animals treated three times per week with rEPO and those of animals treated once weekly with pm25 were substantially identical (see Table 8).

TABLE 8

Long-term In Vivo Bio-Assay Results

| Sample | Treatment | Hematocrit Pretreated | Final | Hemoglobulin (g/dl) Pretreated | Final |
|---|---|---|---|---|---|
| EPO | 200 units/kg TIW | 37.8 | 41.5 | 10.3 | 11.5 |
| pm25 | 240 units/kg QW | 37.7 | 40.8 | 10.2 | 11.2 |

EXAMPLE 9

Structural Characterization of Expressed Proteins

A. Protease Lys-C Digestion of Purified rEPO and pm25 rEPO and pm25 were digested with Lys-C (K. L. Stone et al., A Practical Guide to Protein and Peptide Purification for Microsequencing, pp. 31–471, ed. P. L. Maztsudaira, Academic Press (1989)), and the resulting peptides were analyzed to map the location of disulfide bonds in these molecules. Typically, 100 micrograms of purified protein was dried into a microcentrifuge tube and the protein dissolved with 50 microliters of 400 mM $NH_4HCO_3$, pH 8.2, 2 mM EDTA, 8M urea (deionized). A second sample of each was reduced prior to Lys-C digestion. Reduction was done with dithiothreitol (DTT) at 4.5 mM for 30 minutes at 37° C. under nitrogen; after reduction, the sample was equilibrated to room temperature and alkylated with 10 mM iodoacetic acid for 1 hour at room temperature under nitrogen and in the dark. The reduced and non-reduced samples were diluted with distilled water to bring the urea concentration to 2M. The proteins were digested with 1.5 micrograms of Lys-C for 2–3 hours at 37° C. under nitrogen, then an additional 1.5 micrograms of enzyme was added and the digestion was continued for 15 hours. The digestion was terminated by addition of TFA to 0.5%. Peptides were isolated by reverse phase high performance liquid chromatography (HPLC) using a uRPC C2/C18 column (2.1×100 mnm) and a SMART system (Pharmacia). The equilibration buffer was 0.1% TFA in 5% $CH_3CN$ and the elution buffer was 0.08% TFA in 80% $CH_3CN$. The flowrate was 200 microliters per minute. Five minutes after loading, a 55 minute gradient elution (from 0 to 100% buffer) was performed. Eluted peaks were collected with the SMART system "peak detection" capability. Fractions were stored at −20° C. prior to amino acid sequencing. The identity of the Lys-C peptides was determined by amino acid sequencing (R. M. Hewick et al., *J. Biol. Chem.* 256:7990–7997 (1981), using an ABI Model 470A or 477A sequenator equipped with an ABI Model 120A PTH analyzer (Applied Biosystems, Inc., Foster City, Calif., USA). Data were collected and analyzed using a PE Nelson software system for amino acid sequence analysis (Access*Chrom, Micro Vax 2000, Cupertino, Calif., USA) with a software package for chromatographic data management.

B. Identification of Disulfide Bond Positions in rEPO and pm25

Figure 4:
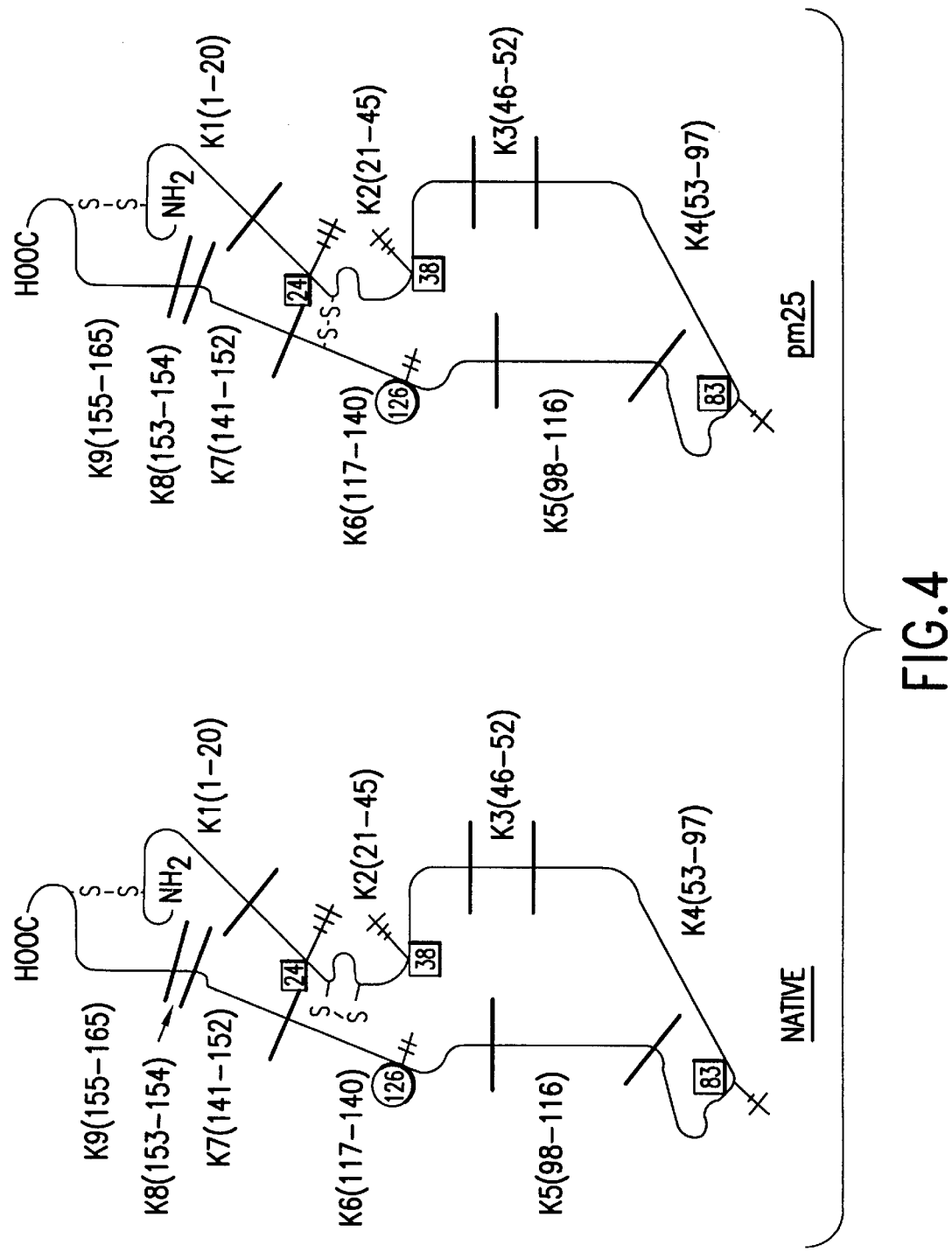
FIG. 4 is a schematic illustration of both native human erythropoietin and pm25.

The deduced amino acid sequence of erythropoietin predicts eight lysine residues in the molecule. The construction of pm25, described in Example 1, does not alter the number or location of the lysine residues. Therefore, both of these molecules should have very similar Lys-C peptides, with any differences arising because of the amino changes at residues 33 and 139 in pm25. The amino acid sequence predicts nine Lys-C peptides should be generated from either rEPO or pm25 when these molecules are digested with this protease. The position of the Lys-C fragments of both molecules are depicted in FIG. 4. The fragments are labelled K1 through K9 with the erythropoietin residues contained within each peptide shown in parentheses. The position of disulfide bonds known to exist in erythropoietin (P. H. Lai et al., *J. Biol. Chem.* 261:3116–3121 (1986)) are included, as well as the probable new disulfide connecting cysteines at residues 29 and 139 in pm25.

Reverse phase chromatography of Lys-C digests of rEPO revealed a pattern closely similar to one previously reported for non-recombinant erythropoietin (HEPO) (M. A. Recny et al., *J. Biol. Chem.* 262:17156–17163 (1967) and consistent with the schematic representation of FIG. 4. The assignment of peptides from the chromatography was based on amino acid sequencing of the peptide fragments. Comparison of the peptide maps of reduced and non-reduced rEPO showed that peptide K1 and K9 co-chromatograph in the unreduced sample and elute at different retention times in the reduced samples. This was taken as clear evidence of a disulfide bond between peptide K1 and K9 in rEPO (and hEPO). Examination of the peptide profiles for reduced and non-reduced pm25 revealed an identical pattern for peptides K1 and K9. However, peptides K2 and K6 also exhibited altered retention times in the reduced and non-reduced samples. Peptide K2 co-chromatographed with K6 in the non-reduced pm25 sample and had a distinctly different retention time in the reduced pm25 sample. This was taken as clear evidence that peptides K2 and K6 are linked by a disulfide bridge as depicted in FIG. 4.

EXAMPLE 10

Preparation of Double Mutants of Erythropoietin

Double mutants of a mammalian erythropoietin, in which a mutation (change in amino acid) at a first position, which causes a significant loss in activity, is compensated for by a mutation at a second position, which is distant from the first position in the primary structure of the protein, such that the activity of the double mutant is significantly greater than that of the mutant with the activity-reducing mutation at the first position, are prepared as described below. In the context of this example, as will be recognized by one skilled in the art, "activity", unless otherwise qualified, refers to specific activity in erythropoiesis in vivo.

A first such double mutant of human erythropoietin is pm25, in which a first mutation, at residue 33, substantially eliminates erythropoietic activity, and a second mutation, the change from Arg to Cys at residue 139, completely restores and possibly even improves erythropoietic activity over that of the wild-type glycohormone. This demonstration, that intramolecular compensating mutations are possible in mammalian erythropoietins, makes available a wide variety of double mutants of that glycohormone, including such double mutants as are substantially improved in erythropoietic activity over that of the corresponding, wild-type glycohormone.

Beginning with a first cDNA encoding a first mutant, which has reduced activity (and typically substantially no activity) because of a change in an amino acid at one position, the skilled practitioner can readily generate very large numbers of second mutants, which differ from the first in having one or more changes in amino acids at second or subsequent positions, and can then expression-screen the second cDNAs encoding the second mutants for those mutants which have the desired level of erythrotropic activity.

The process will be illustrated with human erythropoietin and for the typical case, in which the first mutant has no erythropoietic activity in vitro. However, it will be readily apparent that the process can be applied with any mammalian erythropoietin and for cases in which the first mutant has activity that is reduced in comparison with the wild-type but not eliminated.

The process entails four steps, beginning with a first cDNA, which encodes a prepro-first mutant of human erythropoietin. Typically, the segment of the cDNA encoding the leader peptide will encode the leader peptide for prepro-human erythropoietin. In a first step, a large number of random mutations in the first cDNA are generated at sites such that any resulting change in amino acid will be at a position, in the primary sequence of the mature glycoprotein, which is distant from the position of the change in amino acid in the first mutant. Even when the mutations are essentially randomly distributed along the entire cDNA encoding the prepro-first mutant, most of them will be in nucleotide triplets (codons) that are outside the leader peptide-encoding segment of the first cDNA and that correspond to amino acids at positions which are distant, in the primary sequence of the mature protein, from the position of the amino acid change in the first, inactive mutant glycohormone. By "distant" is meant a separation of at least 1 and more typically at least 10 amino acid positions.

Second, the repertoire of randomly-mutated second cDNAs from the first step is ligated for cloning into an eukaryotic expression vector and the resulting library ("random library") of vectors harboring the randomly-mutated second cDNAs is cloned in a suitable host to prepare a convenient quantity of vectors of the library.

Third, the random library is transfected into eukaryotic cells (e.g., CHO cells or other suitable mammalian cells), in which the randomly-mutated second cDNAs in the expression vectors of the libraty are capable of being expressed and processed to secrete mature, second mutants. The cells are then cultured, and the resulting cell population is screened to isolate single-cell clones which produce erythropoietin activity in an in vitro assay for such activity. The clones with such activity are those which produce an erythropoietin analog which is a second mutant wherein a second mutation compensates for the lack of activity in the first mutant.

Fourth, the second cDNA, encoding the erythropoietin second mutant from a clone producing the same, is amplified as by the polymerase-chain-reaction ("PCR") or any other nucleic acid amplification technique, and the amplified nucleic acid is sequenced to determine the position and amino acid change of the second, compensating mutation. While it is possible that a "compensating mutation" produced in a process which randomly mutates the prepro-first mutant-encoding cDNA, as just described, could entail changes in amino acids at more than one position, or an addition or deletion of an amino acid, it is probable that such a mutation would entail a change in an amino acid at only one position.

The resulting, newly identified, double-mutanterythropoietin-encoding cDNA is then used, in a suitable eukaryotic expression vector, to produce the double mutant glycohormone by culturing mammalian cells transformed with the vector, and the double-mutant so produced is tested for in vivo specific activity in a suitable animal model, such as that described for pm25 above.

A process of mutagenesis by PCR is one procedure by which a second mutation that leads to a compensating amino acid change can be introduced at a site distant from the site of a first mutation in the native protein. In such a process, the 3'-ends of the two PCR primers bracket the segment of the cDNA in which it is intended to introduce the second mutation, and one of the PCT primers anneals to a segment which includes the first mutation and, consequently, protects the first mutation from further mutation in the PCR process. The first cDNA's segments, to one strand of which the primers anneal for primer extension, are protected from mutagenesis. Mutations are introduced randomly into the segment of the first cDNA that is bracketed by the 3'-ends of the primers. The greater the distance between the primers, the greater the region of the first cDNA (encoding the inactive or reduced-activity first mutant) which is exposed to mutation which will introduce a compensating, intramolecular mutation of amino acid in the glycohormone. Each of the primers either includes one strand of a restriction site or anneals to a segment of the first cDNA which includes one strand of a restriction site in order to facilitate introduction of PCR-amplified fragments into expression vectors for expression of any prepro-double mutants of erythropoietin. The PCR process is carried out under conditions which favor mistakes in nucleotide incorporation. Such conditions include use of three of the 2'-deoxyribonucleoside-5'-triphosphates at 1 mM concentration and the fourth at 200 $\mu$M concentration with 0.5 mM $Mn^{+2}$, 6 mM $Mg^{+2}$, and Taq polymerase in the PCR amplification reaction mixture.

More specifically, the process is carried out with reference to the double mutant pm25 as follows: A first cDNA encoding an inactive or reduced-activity erythropoietin analog, such as one having a Cys-to-Pro mutation at position 33, is used as a template for starting the mutagenesis using PCR. One such first cDNA has the sequence which differs from that shown in SEQ ID NO:1 only by having CC at positions 199 and 200. Using this first cDNA for illustration, a first PCR primer is used which hybridizes to a segment, including the CC at positions 199 and 200, of the strand of the cDNA which has (except at positions 199–200) the sequence shown in SEQ ID NO:1. Also, a second primer is used which hybridizes to that strand of the cDNA to which the first primer does not anneal. The second primer anneals to a segment of this strand which has its 3'-end base-paired to a base pair that is at a position located 3' of base 517 as illustrated in SEQ ID NO:1. Thus, in the PCR mutagenesis process, it is possible that the base pair of the first cDNA corresponding to base 517 in SEQ ID NO:1 can be mutagenized to a T, which will convert the triplet 517–519 to one coding for Cys.

The PCR-mutagenized products, which include some sequences with random mutations between the primers defining the ends of the amplified product, are then digested with restriction enzymes using sites incorporated into the PCR product as suggested above. The fragments from the digestion which are of a size that includes those with the random mutations are then ligated into a suitable eukaryotic expression vector, operably for expression and secretion from a mammalian cell in culture of the doubly mutated erythropoietin analogs. Such an expression vector will provide a mammalian (in this case, preferably human) erythropoietin leader peptide at the amino-terminus of the mature, double mutants which provides for their glycosylation and secretion and, of course, will provide appropriate signals for transcription and other steps necessary for expression of the preproerythropoietin double mutants in a mammalian cell. The vector will also be suitable for cloning to provide sufficient qualities of the vector for mammalian cell transfection and other uses. For example, the PCR-amplified fragments can first be ligated to fragments which code for parts of preproerythropoietin, providing fragments with cDNA coding for full-length preproerythropoietin double mutants. These fragments, coding for full-length protein, can then be ligated into a vector such as SV2dhfrSVdeltaSJneo to provide suitable expression vectors for the double mutants.

The resulting library of expression vectors, with the doubly mutated cDNAs incorporated, is then cloned in a suitable host, such as *E. coli*, to obtain sufficient amounts of the library for further work.

The library of expression vectors, with the doubly mutated cDNAs, is transfected into mammalian cells (e.g., CHO cells) as described above in Example 2. The cells are cultured as single-cell clones or colonies of small numbers (e.g., about 10) of cells. Each culture is then screened for in vitro erythrotropic activity. The only cultures which will screen positively (for such in vitro activity) will be those in which an erythropoietin analog is expressed which has a second, random mutation compensating for the attenuation of activity caused by the first (e.g., $Cys^{33}$-to-$Pro^{33}$) mutation. Cultures which show activity but were grown from more than one cell can be subcultured as single-cell clones to isolate cells that produce doubly-mutated, active analogs.

Analog-encoding cDNA can be isolated from cells producing biologically active glycohormone and then sequenced by standard techniques to identify the second, compensating mutations in the erythropoietins from such cells.

The cells producing biologically active glycohormone can be cultured, and the glycohormone can be isolated and purified from the culture media and then tested for in vivo erythropropic activity in a suitable animal model, as described above. Thus, double mutant analogs can be found which have enhanced pharmaceutical utility due to increased potency, prolonged half-life, or the like.

It will be recognized that a double mutant of erythropoietin, which has a compensating mutation restoring in vivo erythropoietic activity to a first, inactive mutant, may be converted to an even more active mutant by elimination of the first, inactivating mutation. Thus, the present invention also provides single-mutation analogs of a mammalian (preferably human) erythropoietin, which have in vivo erythropoietic activity. Such a single-mutation analogs of the invention have a single, first change in an amino acid from the sequence of the mature wild-type glycohormone wherein said first change, when made in an analog which has a single, second amino acid change from the sequence of, and in vivo erythropoietic activity less than that of, the wild-type glycohormone, increases the in vivo erythropoietic activity of the single-mutation analog with the single, second amino acid change. A paradigm of such a single-mutation analog of the invention is the $[Cys^{139}]$ analog of human erythropoietin.

While examples of the present invention have been described above with specificity, it is intended that modifications and variations of what has been described, which are readily apparent to those skilled in the pertinent arts, will be within the spirit of the invention and thus within the scope thereof, which is defined exclusively by the claims which follow.

What is claimed is:

1. An analog of human erythropoietin which has an amino acid sequence selected from the group consisting of the sequences of ($X^{33}$, $Cys^{139}$)-human erythropoietin and ($X^{33}$, $Cys^{139}$, des-$Arg^{166}$)-human erythropoietin, wherein $X^{33}$ is selected from the group consisting of Pro and Cys.

2. The analog according to claim 1 which is des-$Arg^{166}$.

3. The analog according to claim 2 wherein $X^{33}$ is Pro.

4. The analog according to claim 2 wherein $X^{33}$ is Cys.

5. A double-stranded DNA which comprises a segment of 498 nucleotides in a sequence which encodes an analog of human erythropoietin having an amino acid sequence selected from the group consisting of the sequences of ($X^{33}$, $Cys^{139}$)-human erythropoietin or a segment of 495 nucleotides in a sequence which encodes an analog of human erythropoietin which has an amino acid sequence selected from the group consisting of the sequences of ($X^{33}$, $Cys^{139}$, des-$Arg^{166}$)-human erythropoietin, wherein $X^{33}$ is selected from the group consisting of Pro and Cys.

6. The double-stranded DNA according to claim 5 wherein $X^{33}$ is Pro.

7. The double-stranded DNA according to claim 5 wherein $X^{33}$ is Cys.

8. The double-stranded DNA according to claim 6 wherein the segment is of 498 nucleotides.

9. The double-stranded DNA according to claim 7 wherein the segment is of 498 nucleotides.

10. The double-stranded DNA according to any one of claims 5–9 wherein the segment of 498 or 495 nucleotides is one of two, contiguous subsegments and the other subsegment encodes a leader peptide of a mammalian preproerythropoietin and is joined to the 498-nucleotide or 495-nucleotide subsegment such that, in a polypeptide encoded by the contiguous subsegments, the carboxy-terminus of the leader peptide is adjacent the amino-terminus of the erythropoietin analog.

11. The double-stranded DNA according to claim 10 wherein the leader peptide encoded by the leader-peptide encoding subsegment has the sequence Mer Gly Val His Glu Cys Pro Ala Trp Leu Trp Leu Leu Leu Ser Leu $X^3$ Ser Leu Pro Leu Gly Leu Pro Val $X^4$ Gly (SEQ ID NO:16), wherein $X^3$ is selected from the group consisting of Leu and Val, and $X^4$ is selected from the group consisting of Leu and Pro.

12. The double-stranded DNA according to claim 11 wherein $X^3$ and $X^4$ are each Leu.

13. An expression vector comprising the double-stranded DNA according to claim 10 for expressing, in a mammalian cell in culture a preproerythropoietin analog having a sequence consisting of the sequence of the leader peptide joined at its carboxy terminus to the amino terminus of the sequence of the analog of human erythropoietin.

14. An expression vector comprising the double-stranded DNA according to claim 11 for expressing, in a mammalian cell in culture, a preproerythropoietin analog having a sequence consisting of the sequence of the leader peptide joined at its carboxy terminus to the amino terminus of the sequence of the analog of human erythropoietin.

15. An expression vector comprising the double-stranded DNA according to claim 12 for expressing, in a mammalian cell in culture, a preproerythropoietin analog having a sequence consisting of the sequence of the leader peptide joined at its carboxy terminus to the amino terminus of the sequence of the analog of human erythropoietin.

16. The expression vector according to claim 15 which consists of SV2dhfrSVdeltaSJneo with, inserted at the XbaI site of that vector operably for expression of a preproerythropoietin analog, a double stranded DNA which comprises a segment which encodes the preproerythropoietin analog.

17. The expression vector SV2dhfrSVdeltaSJneo(Pro$^{33}$, Cys$^{139}$)hEPO).

18. The expression vector SV2dhfrSVdeltaSJneo ((Cys$^{139}$)hEPO).

19. A mammalian cell in culture which comprises an expression vector for expression, in said cell, of a DNA consisting of two contiguous segments which together encode a precursor polypeptide, said precursor polypeptide consisting of a leader peptide of a mammalian preproerythropoietin joined at its carboxy-terminus to the amino terminus of an human erythropoietin analog, one of said segments encoding said leader peptide, the other of said segments having 498 base pairs and encoding said erythropoietin analog which analog has a sequence selected from the group consisting of the sequences of ($X^{33}$, Cys$^{139}$)-human erythropoietin, wherein $X^{33}$ is selected from the group consisting of Pro and Cys.

20. The mammalian cell according to claim 19 which is dhfr-, wherein the expression vector consists of SV2dhfrSVdeltaSJneo with, inserted at the XbaI site of that vector operably for expression of a preproerythropoietin, said DNA consisting of two contiguous segments.

21. The mammalian cell according to claim 20 which is a Chinese hamster ovary cell, wherein the expression vector is selected from the group consisting of SV2dhfrSVdeltaSJneo ((Pro$^{33}$, Cys$^{139}$)hEPO) and SV2dhfrSVdeltaSJneo((Cys$^{139}$) hEPO).

22. A pharmaceutical composition useful for inducing erythropoiesis, comprising (a) a therapeutically effective amount of an analog of human erythropoietin which has an amino acid sequence selected from the group consisting of the sequences of ($X^{33}$, Cys$^{139}$, des-Arg$^{166}$)-human erythropoietin, wherein $X^{33}$ is selected from the group consisting of Pro and Cys, in combination with (b) a pharmaceutically acceptable carrier.

23. The pharmaceutical composition according to claim 22 wherein $X^{33}$ is Pro.

24. The pharmaceutical composition according to claim 22 wherein $X^{33}$ is Cys.

25. A pharmaceutical composition useful for treating anemia, comprising (a) a therapeutically effective amount of an analog of human erythropoietin which has an amino acid sequence selected from the group consisting of the sequences of ($X^{33}$, Cys$^{139}$, des-Arg$^{166}$)-human erythropoietin, wherein $X^{33}$ is selected from the group consisting of Pro and Cys, in combination with (b) a pharmaceutically acceptable carrier.

26. The pharmaceutical composition according to claim 25 wherein $X^{33}$ is Pro.

27. The pharmaceutical composition according to claim 25 wherein $X^{33}$ is Cys.

* * * * *

UNITED STATES PATENT AND TRADEMARK OFFICE
CERTIFICATE OF CORRECTION

PATENT NO. : 5,888,772
DATED : March 30, 1999
INVENTOR(S) : Gregory F. Okasinski et al.

It is certified that error appears in the above-indentified patent and that said Letters Patent is hereby corrected as shown below:

On title page, item 54 Title
replace "DNA ENCODING HUMAN A ERYTHROPOIETIN ANALOG"
with --DNA ENCODING A HUMAN ERYTHROPOIETIN ANALOG--.

Col. 35, line 63
replace "des-Arg$^{166}$"
with --($X^{33}$, $Cys^{139}$, des-Arg$^{166}$)--.

Col. 37, line 18
replace "Mer"
with --Met--.

Signed and Sealed this

Seventeenth Day of April, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 625 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:1:

```
GGATCCCCGC  CAGGCGCCAC  C ATG GGG GTG CAC GAA TGT CCT GCC              4 5
                          Met Gly Val His Glu Cys Pro Ala
                              -25                     -20

TGG CTG TGG CTT CTC CTG TCC CTG CTG TCG CTC CCT CTG GGC                8 7
Trp Leu Trp Leu Leu Leu Ser Leu Leu Ser Leu Pro Leu Gly
```

|  |  |  |  |  | -15 |  |  |  |  | -10 |  |  |  |  |
|---|---|---|---|---|---|---|---|---|---|---|---|---|---|---|
| CTC | CCA | GTA | CTG | GGC | GCC | CCA | CCA | CGC | CTC | ATA | TGT | GAC | TCG | 129 |
| Leu | Pro | Val | Leu | Gly | Ala | Pro | Pro | Arg | Leu | Ile | Cys | Asp | Ser |  |
| -5 |  |  |  |  | 1 |  |  |  | 5 |  |  |  |  |  |
| CGA | GTC | CTC | GAG | AGG | TAC | CTC | TTG | GAG | GCC | AAG | GAG | GCC | GAG | 171 |
| Arg | Val | Leu | Glu | Arg | Tyr | Leu | Leu | Glu | Ala | Lys | Glu | Ala | Glu |  |
| 10 |  |  |  |  | 15 |  |  |  |  | 20 |  |  |  |  |
| AAT | ATT | ACG | ACG | GGC | TGT | GCT | GAG | CAC | TGC | AGC | TTG | AAT | GAG | 213 |
| Asn | Ile | Thr | Thr | Gly | Cys | Ala | Glu | His | Cys | Ser | Leu | Asn | Glu |  |
|  | 25 |  |  |  |  |  | 30 |  |  |  |  | 35 |  |  |
| AAT | ATC | ACT | GTC | CCA | GAC | ACC | AAA | GTT | AAC | TTC | TAT | GCA | TGG | 255 |
| Asn | Ile | Thr | Val | Pro | Asp | Thr | Lys | Val | Asn | Phe | Tyr | Ala | Trp |  |
|  |  | 40 |  |  |  |  | 45 |  |  |  |  |  | 50 |  |
| AAG | AGA | ATG | GAG | GTC | GGG | CAG | CAG | GCC | GTA | GAA | GTC | TGG | CAG | 297 |
| Lys | Arg | Met | Glu | Val | Gly | Gln | Gln | Ala | Val | Glu | Val | Trp | Gln |  |
|  |  |  | 55 |  |  |  |  |  | 60 |  |  |  |  | 65 |
| GGC | CTG | GCC | CTG | CTG | TCG | GAA | GCT | GTT | CTG | CGG | GGC | CAG | GCC | 339 |
| Gly | Leu | Ala | Leu | Leu | Ser | Glu | Ala | Val | Leu | Arg | Gly | Gln | Ala |  |
|  |  |  |  |  | 70 |  |  |  |  |  | 75 |  |  |  |
| CTG | TTG | GTC | AAT | TCC | TCC | CAG | CCG | TGG | GAG | CCC | CTG | CAG | CTG | 381 |
| Leu | Leu | Val | Asn | Ser | Ser | Gln | Pro | Trp | Glu | Pro | Leu | Gln | Leu |  |
| 80 |  |  |  |  | 85 |  |  |  |  |  | 90 |  |  |  |
| CAT | GTG | GAT | AAA | GCC | GTC | AGT | GGC | CTT | CGC | AGC | CTC | ACC | ACT | 423 |
| His | Val | Asp | Lys | Ala | Val | Ser | Gly | Leu | Arg | Ser | Leu | Thr | Thr |  |
|  | 95 |  |  |  | 100 |  |  |  |  | 105 |  |  |  |  |
| CTG | CTT | CGA | GCT | CTG | GGG | GCC | CAG | AAG | GAA | GCC | ATC | TCC | CCT | 465 |
| Leu | Leu | Arg | Ala | Leu | Gly | Ala | Gln | Lys | Glu | Ala | Ile | Ser | Pro |  |
|  |  | 110 |  |  |  |  | 115 |  |  |  |  | 120 |  |  |
| CCA | GAT | GCG | GCC | TCA | GCT | GCT | CCA | CTC | CGA | ACA | ATC | ACT | GCT | 507 |
| Pro | Asp | Ala | Ala | Ser | Ala | Ala | Pro | Leu | Arg | Thr | Ile | Thr | Ala |  |
|  |  |  | 125 |  |  |  |  |  | 130 |  |  |  |  | 135 |
| GAC | ACT | TTC | CGC | AAA | CTC | TTC | CGA | GTC | TAC | TCC | AAT | TTC | CTC | 549 |
| Asp | Thr | Phe | Arg | Lys | Leu | Phe | Arg | Val | Tyr | Ser | Asn | Phe | Leu |  |
|  |  |  |  | 140 |  |  |  |  | 145 |  |  |  |  |  |
| CGC | GGA | AAG | CTG | AAG | CTT | TAC | ACA | GGG | GAG | GCA | TGC | AGG | ACA | 591 |
| Arg | Gly | Lys | Leu | Lys | Leu | Tyr | Thr | Gly | Glu | Ala | Cys | Arg | Thr |  |
| 150 |  |  |  |  | 155 |  |  |  |  | 160 |  |  |  |  |
| GGG | GAC | AGA | TGATGACCAG | GTGTTACCTG | GATCC |  |  |  |  |  |  |  |  | 625 |
| Gly | Asp | Arg |  |  |  |  |  |  |  |  |  |  |  |  |
|  | 165 |  |  |  |  |  |  |  |  |  |  |  |  |  |

( 2 ) INFORMATION FOR SEQ ID NO:2:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:2:

CCCTGTTGGT CAATTCCTCC CAGCCGTG                28

( 2 ) INFORMATION FOR SEQ ID NO:3:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:3:

CCTGCAGCTG CATGTGGATA AAGCCGTCAG 30

( 2 ) INFORMATION FOR SEQ ID NO:4:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:4:

GCTGTGCTGA GCACCCCAGC TTGAATGAGA AT 32

( 2 ) INFORMATION FOR SEQ ID NO:5:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:5:

ACTGCTGACA CTTTCTGCAA ACTCTTCCGA GT 32

( 2 ) INFORMATION FOR SEQ ID NO:6:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Met Gly Val His Glu Cys Pro Ala Trp Leu Trp Leu Leu Leu
                5                                10

Ser Leu Leu Ser Leu Pro Leu Gly Leu Pro Val Leu Gly
15                      20                      25

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Met Gly Val His Glu Cys Pro Ala Trp Leu Trp Leu Leu Leu
                5                                10

Ser Leu Val Ser Leu Pro Leu Gly Leu Pro Val Pro Gly
15                      20                      25

( 2 ) INFORMATION FOR SEQ ID NO:8:

( i ) SEQUENCE CHARACTERISTICS:
        ( A ) LENGTH: 85 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:8:

AGCTTGTGTG GATCCCCGCC AGGCGCCACC ATGGGGGTGC ACGAATGTCC           50

TGCCTGGCTG TGGCTTCTCC TGTCCCTGCT GTCGC                           85

( 2 ) INFORMATION FOR SEQ ID NO:9:

( i ) SEQUENCE CHARACTERISTICS:
        ( A ) LENGTH: 82 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:9:

TCGCTCCCTC TGGGCCTCCC AGTACTGGGC GCCCCACCAC GCCTCATATG           50

TGACTCGCGA GTCCTCGAGA GGTACCTCTT GG                              82

( 2 ) INFORMATION FOR SEQ ID NO:10:

( i ) SEQUENCE CHARACTERISTICS:
        ( A ) LENGTH: 85 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:10:

TTGGAGGCCA AGGAGGCCGA GAATATTACG ACGGGCTGTG CTGAGCACTG           50

CAGCTTGAAT GAGAATATCA CTGTCCCAGA CACCA                           85

( 2 ) INFORMATION FOR SEQ ID NO:11:

( i ) SEQUENCE CHARACTERISTICS:
        ( A ) LENGTH: 82 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:11:

ACCAAAGTTA ACTTCTATGC ATGGAAGAGA ATGGAGGTCG GGCAGCAGGC           50

CGTAGAAGTC TGGCAGGGCC TGGCCCTGCT GT                              82

( 2 ) INFORMATION FOR SEQ ID NO:12:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:12:

CTGTCGGAAG CTGTTCGGCG GGGCCAGGCC CTGTTGGTCA ATCTCTCCCA           50

GCCGTGGGAG CCCCTGCAGC TGCATCTAG                                  79

( 2 ) INFORMATION FOR SEQ ID NO:13:

-continued ( i ) SEQUENCE CHARACTERISTICS:
    ( A ) LENGTH: 88 bases
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:13:

```
CTAGATAAAG  CCGTCAGTGG  CCTTCGCAGC  CTCACCACTC  TGCTTCGAGC              50
TCTGGGGGCC  CAGAAGGAAG  CCATCTCCCC  TCCAGATG                            88
```

( 2 ) INFORMATION FOR SEQ ID NO:14:

( i ) SEQUENCE CHARACTERISTICS:
    ( A ) LENGTH: 82 bases
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:14:

```
GATGCGGCCT  CAGCTGCTCC  ACTCCGAACA  ATCACTGCTG  ACACTTTCCG              50
CAAACTCTTC  CGAGTCTACT  CCAATTTCCT  CC                                  82
```

( 2 ) INFORMATION FOR SEQ ID NO:15:

( i ) SEQUENCE CHARACTERISTICS:
    ( A ) LENGTH: 85 bases
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:15:

```
CTCCGCGGAA  AGCTGAAGCT  TTACACAGGG  GAGGCATGCA  GGACAGGGGA              50
CAGATGATGA  CCAGGTGTTA  CCTGGATCCT  GAATT                               85
```

( 2 ) INFORMATION FOR SEQ ID NO:16:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:16:

```
Met  Gly  Val  His  Glu  Cys  Pro  Ala  Trp  Leu  Trp  Leu  Leu  Leu
                         5                        10
Ser  Leu  Xaa  Ser  Leu  Pro  Leu  Gly  Leu  Pro  Val  Xaa  Gly
15                       20                       25
```